United States Patent
Padilla et al.

(10) Patent No.: US 10,085,958 B2
(45) Date of Patent: Oct. 2, 2018

(54) BROMFENAC BIOAVAILABILITY

(71) Applicants: Angel Padilla, Aliso Viejo, CA (US); George Baklayan, Huntington Beach, CA (US)

(72) Inventors: Angel Padilla, Aliso Viejo, CA (US); George Baklayan, Huntington Beach, CA (US)

(73) Assignee: BAUSCH & LOMB PHARMA HOLDINGS CORP., Rochester, NY (US)

( * ) Notice: Subject to any disclaimer, the term of this patent is extended or adjusted under 35 U.S.C. 154(b) by 39 days.

(21) Appl. No.: 15/343,457

(22) Filed: Nov. 4, 2016

(65) Prior Publication Data

US 2017/0049735 A1 Feb. 23, 2017

Related U.S. Application Data

(62) Division of application No. 13/649,271, filed on Oct. 11, 2012, now Pat. No. 9,517,220.

(60) Provisional application No. 61/546,290, filed on Oct. 12, 2011.

(51) Int. Cl.
| | |
|---|---|
| A61K 31/196 | (2006.01) |
| A61K 9/48 | (2006.01) |
| A61K 31/14 | (2006.01) |
| A61K 31/79 | (2006.01) |
| A61K 31/775 | (2006.01) |
| A61K 33/04 | (2006.01) |
| A61K 47/02 | (2006.01) |
| A61K 47/24 | (2006.01) |
| A61K 47/32 | (2006.01) |
| A61K 9/00 | (2006.01) |
| A61K 47/18 | (2017.01) |

(52) U.S. Cl.
CPC .......... *A61K 31/196* (2013.01); *A61K 9/0048* (2013.01); *A61K 31/14* (2013.01); *A61K 31/775* (2013.01); *A61K 31/79* (2013.01); *A61K 33/04* (2013.01); *A61K 47/02* (2013.01); *A61K 47/186* (2013.01); *A61K 47/24* (2013.01); *A61K 47/32* (2013.01)

(58) Field of Classification Search
CPC ............................ A61K 31/196; A61K 9/0048
See application file for complete search history.

(56) References Cited

U.S. PATENT DOCUMENTS

| | | | |
|---|---|---|---|
| 5,558,876 A * | 9/1996 | Desai | A61K 9/0048 424/422 |
| 2005/0239895 A1 | 10/2005 | Sawa et al. | |
| 2007/0287749 A1 | 12/2007 | Sawa et al. | |
| 2007/0297981 A1 | 12/2007 | Ousler, III et al. | |
| 2007/0299124 A1 | 12/2007 | Ousler, III et al. | |
| 2008/0039398 A1 | 2/2008 | Ousler, III et al. | |
| 2008/0070908 A1 | 3/2008 | Muller et al. | |
| 2010/0008993 A1 | 1/2010 | Proksch et al. | |
| 2010/0227928 A1 | 9/2010 | Hosseini et al. | |
| 2011/0054031 A1 | 3/2011 | McNamara et al. | |

FOREIGN PATENT DOCUMENTS

| | | |
|---|---|---|
| EP | 0 856 316 | 8/1998 |
| WO | 2011/058579 | 5/2011 |
| WO | 2011/127196 | 10/2011 |

OTHER PUBLICATIONS

International Search Report and Written Opinion, PCT/US2012/059653, dated Dec. 4, 2012 (12 pages).
International Preliminary Report on Patentability, PCT/US2012/059653, dated Jan. 16, 2014 (6 pages).

* cited by examiner

*Primary Examiner* — Sreeni Padmanabhan
*Assistant Examiner* — Jody Karol
(74) *Attorney, Agent, or Firm* — Thompson Hine LLP

(57) ABSTRACT

Formulations and methods that provided enhanced bromfenac penetration into ocular tissue when topically administered, compared to the currently available BROMDAY™ formulation and method when topically administered. The formulations and methods did so while retaining the patient convenience of a once-daily administration and advantageously lowered the bromfenac concentration dosed to the patient.

13 Claims, 22 Drawing Sheets

BROMFENAC BIOAVAILABILITY

This application is a division of co-pending U.S. application Ser. No. 13/649,271 filed Oct. 11, 2012, which claims the benefit of U.S. Provisional Application Ser. No. 61/546,290 filed Oct. 12, 2011, both of which are expressly incorporated by reference herein in their entirety.

Bromfenac, 2-amino-3-(4-bromobenzoyl)phenylacetic acid, is a non-steroidal antiinflammatory drug (NSAID) and has use as a topical ophthalmic solution, e.g., administrating to patients for treating pain and inflammation associated with ocular surgery. BROMDAY™ is a commercially available topical ophthalmic bromfenac 0.09% solution. Bromfenac formulations and methods of use are disclosed in U.S. Published Patent Application Nos. 20050239895, 20070287749, and 20110054031 each of which is expressly incorporated by reference in its entirety herein.

Bromfenac's anti-inflammatory effect is by its known action as a blocker of prostaglandin synthesis. In the front of the eye, the iris and ciliary body are known sites of prostaglandin synthesis that regulate ocular inflammatory processes; the front of the eye encompasses the anterior chamber, the iris, and the ciliary body, while the back of the eye encompasses the retina, the choroid, and scleral tissue located near the back of the eye.

The inventive bromfenac formulations and methods disclosed were similar to the BROMDAY™ formulation but advantageously enhanced bromfenac bioavailability in ocular tissues. For example, in one embodiment, the bromfenac concentration was reduced from 0.09%, and the pH was reduced from pH 8.3 to a lower limit of pH 6.0. In one embodiment, tyloxapol was included in the formulations. In one embodiment, the bromfenac concentration was increased from 0.09%, and the pH was reduced from pH 8.3 to a lower limit of pH 6.0. The enhancement in bromfenac bioavailability afforded by the inventive formulations and methods permitted alterations in bromfenac concentrations to be administered, while still providing comparable or better efficacy than with once-daily topical ocular BROMDAY™ administration.

Figure 1A:
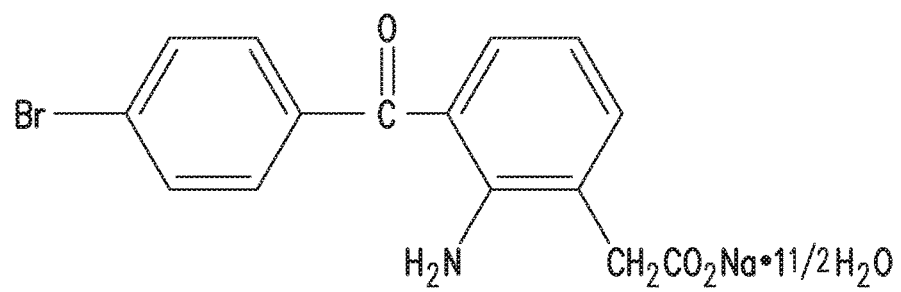
FIG. 1A shows the chemical structure of bromfenac-sodium sesquihydrate.

One embodiment of the method enhances ocular bioavailability of bromfenac in an aqueous solution topically administered to an eye of a patient in need of treatment. A bromfenac formation having pH between pH≥6.0 and pH<8.3 is topically administered to an eye of a patient in need of treatment, e.g., before and/or after cataract surgery. The method results in pH-effected enhanced bromfenac bioavailability in treating the patient. The formulation, due to its lower pH, is less irritating to the patients ocular tissue. In one embodiment, bromfenac in the formulation is <0.09% bromfenac. Throughout this specification and claims, unless otherwise indicated, % (or percent) is on a weight per volume (g/mL) basis.

Unless otherwise stated, all percentage concentrations are w/v. One embodiment of the method treats a patient in need of such treatment with bromfenac at a concentration <0.20%, with bromfenac concentrations provided as the free-acid form. In the method, a bromfenac formulation with pH≥6.0 and pH<8.3, and bromfenac between 0.02% and <0.20% in one embodiment, bromfenac between 0.03% and <0.20% in one embodiment, bromfenac between 0.04% and <0.20% in one embodiment, bromfenac between 0.05% and <0.20% in one embodiment, bromfenac between 0.06% and <0.20% in one embodiment, bromfenac between 0.07% and <0.20% in one embodiment, bromfenac between 0.08% and <0.20% in one embodiment, bromfenac between 0.09% and <0.20% in one embodiment, bromfenac between 0.10% and <0.20% in one embodiment, bromfenac between 0.11% and <0.20% in one embodiment, bromfenac between 0.12% and <0.20% in one embodiment, bromfenac between 0.13% and <0.20% in one embodiment, bromfenac between 0.14% and <0.20% in one embodiment, bromfenac between 0.15% and <0.20% in one embodiment, bromfenac between 0.16% and <0.20% in one embodiment, bromfenac between 0.17% and <0.20% in one embodiment, bromfenac between 0.18% and <0.20% in one embodiment, and bromfenac between 0.19% and <0.20% in one embodiment, is topically administered to the patient's eye under conditions to result in comparable bromfenac efficacy as obtained in studies with bromfenac 0.09%, pH 8.3 under the same administration conditions (e.g., once-daily dosing, the day prior to surgery and 14 days after surgery, etc.). In any of these embodiments, the pH may be between pH≥6.0 and <pH 8.3, i.e., pH 6.0, pH 6.1, pH 6.2, pH 6.3, pH 6.4, pH 6.5; pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, and pH>8.2 up to but excluding pH 8.3.

One embodiment of the method treats ocular pain and/or ocular inflammation from any cause. Such pain and/or inflammation may be due, e.g., to one or a combination of meibomianitis, blepharitis, uveitis, iritis, conjunctival hyperemia, eyelid hyperemia, keratitis, ocular rosacea, scleritis, wet age related macular degeneration, diabetic retinopathy, diabetic macular edema, central retinal vein occlusion, branch retinal vein occlusion, anterior chamber inflammation, allergic conjunctivitis, conjunctivitis, surgical trauma, dry eye, viral conjunctivitis, bacterial conjunctivitis, anterior uveitis, penetration from a foreign body, and/or burns (chemical, radiation, or thermal). One embodiment of the method treats a patient for post-cataract surgery pain and inflammation with bromfenac by topically administering once-daily an aqueous bromfenac formulation at pH between pH≥6.0 and pH<8.3 having a bromfenac concentration between 0.02% to <0.20% bromfenac. In one embodiment, treatment starts with once daily administration the day before surgery and continues with once daily administration to day 14 after surgery.

In one embodiment of the formulation administered, pH is 8.2 and bromfenac is 0.02%.

In one embodiment of the formulation administered, pH is 8.1 and bromfenac is 0.02%. In one embodiment of the formulation administered, pH is 8.0 and bromfenac is 0.02%. In one embodiment of the formulation administered, pH is 7.9 and bromfenac is 0.02%. In one embodiment of the formulation administered, pH is 7.8 and bromfenac is 0.02%. In one embodiment of the formulation administered, pH is 7.7 and bromfenac is 0.02%. In one embodiment of the formulation administered, pH is 7.6 and bromfenac is 0.02%. In one embodiment of the formulation administered, pH is 7.5 and bromfenac is 0.02%. In one embodiment of the formulation administered, pH is 7.4 and bromfenac is 0.02%. In one embodiment of the formulation administered, pH is 7.3 and bromfenac is 0.02%. In one embodiment of the formulation administered, pH is 7.2 and bromfenac is 0.02%. In one embodiment of the formulation administered, pH is 7.1 and bromfenac is 0.02%. In one embodiment of the formulation administered, pH is 7.0 and bromfenac is 0.02%. In one embodiment of the formulation administered, pH is 6.9 and bromfenac is 0.02%. In one embodiment of the formulation administered, pH is 6.8 and bromfenac is 0.02%. In one embodiment of the formulation administered, pH is 6.7 and bromfenac is 0.02%. In one embodiment of the formulation administered, pH is 6.6 and bromfenac is 0.02%. In one embodiment of the formulation administered, pH is 6.5 and bromfenac is 0.02%. In one embodiment of the formulation administered, pH is 6.4 and bromfenac is 0.02%. In one embodiment of the formulation administered, pH is 6.3 and bromfenac is 0.02%. In one embodiment of the formulation administered, pH is 6.2 and bromfenac is 0.02%. In one embodiment of the formulation administered, pH is 6.1 and bromfenac is 0.02%. In one embodiment of the formulation administered, pH is 6.0 and bromfenac is 0.02%.

In one embodiment of the formulation administered, pH is 8.2 and bromfenac is 0.03%. In one embodiment of the formulation administered, pH is 8.1 and bromfenac is 0.03%. In one embodiment of the formulation administered, pH is 8.0 and bromfenac is 0.03%. In one embodiment of the formulation administered, pH is 7.9 and bromfenac is 0.03%. In one embodiment of the formulation administered, pH is 7.8 and bromfenac is 0.03%. In one embodiment of the formulation administered, pH is 7.7 and bromfenac is 0.03%. In one embodiment of the formulation administered, pH is 7.6 and bromfenac is 0.03%. In one embodiment of the formulation administered, pH is 7.5 and bromfenac is 0.03%. In one embodiment of the formulation administered, pH is 7.4 and bromfenac is 0.03%. In one embodiment of the formulation administered, pH is 7.3 and bromfenac is 0.03%. In one embodiment of the formulation administered, pH is 7.2 and bromfenac is 0.03%. In one embodiment of the formulation administered, pH is 7.1 and bromfenac is 0.03%. In one embodiment of the formulation administered, pH is 7.0 and bromfenac is 0.03%. In one embodiment of the formulation administered, pH is 6.9 and bromfenac is 0.03%. In one embodiment of the formulation administered, pH is 6.8 and bromfenac is 0.03%. In one embodiment of the formulation administered, pH is 6.7 and bromfenac is 0.03%. In one embodiment of the formulation administered, pH is 6.6 and bromfenac is 0.03%. In one embodiment of the formulation administered, pH is 6.5 and bromfenac is 0.03%. In one embodiment of the formulation administered, pH is 6.4 and bromfenac is 0.03%. In one embodiment of the formulation administered, pH is 6.3 and bromfenac is 0.03%. In one embodiment of the formulation administered, pH is 6.2 and bromfenac is 0.03%. In one embodiment of the formulation administered, pH is 6.1 and bromfenac is 0.03%. In one embodiment of the formulation administered, pH is 6.0 and bromfenac is 0.03%.

In one embodiment of the formulation administered, pH is 8.2 and bromfenac is 0.04%. In one embodiment of the formulation administered, pH is 8.1 and bromfenac is 0.04%. In one embodiment of the formulation administered, pH is 8.0 and bromfenac is 0.04%. In one embodiment of the formulation administered, pH is 7.9 and bromfenac is 0.04%. In one embodiment of the formulation administered, pH is 7.8 and bromfenac is 0.04%. In one embodiment of the formulation administered, pH is 7.7 and bromfenac is 0.04%. In one embodiment of the formulation administered, pH is 7.6 and bromfenac is 0.04%. In one embodiment of the formulation administered, pH is 7.5 and bromfenac is 0.04%. In one embodiment of the formulation administered, pH is 7.4 and bromfenac is 0.04%. In one embodiment of the formulation administered, pH is 7.3 and bromfenac is 0.04%. In one embodiment of the formulation administered, pH is 7.2 and bromfenac is 0.04%. In one embodiment of the formulation administered, pH is 7.1 and bromfenac is 0.04%. In one embodiment of the formulation administered, pH is 7.0 and bromfenac is 0.04%. In one embodiment of the formulation administered, pH is 6.9 and bromfenac is 0.04%. In one embodiment of the formulation administered, pH is 6.8 and bromfenac is 0.04%. In one embodiment of the formulation administered, pH is 6.7 and bromfenac is 0.04%. In one embodiment of the formulation administered, pH is 6.6 and bromfenac is 0.04%. In one embodiment of the formulation administered, pH is 6.5 and bromfenac is 0.04%. In one embodiment of the formulation administered, pH is 6.4 and bromfenac is 0.04%. In one embodiment of the formulation administered, pH is 6.3 and bromfenac is 0.04%. In one embodiment of the formulation administered, pH is 6.2 and bromfenac is 0.04%. In one embodiment of the formulation administered, pH is 6.1 and bromfenac is 0.04%. In one embodiment of the formulation administered, pH is 6.0 and bromfenac is 0.04%.

In one embodiment of the formulation administered, pH is 8.2 and bromfenac is 0.05%. In one embodiment of the formulation administered, pH is 8.1 and bromfenac is 0.05%. In one embodiment of the formulation administered, pH is 8.0 and bromfenac is 0.05%. In one embodiment of the formulation administered, pH is 7.9 and bromfenac is 0.05%. In one embodiment of the formulation administered, pH is 7.8 and bromfenac is 0.05%. In one embodiment of the formulation administered, pH is 7.7 and bromfenac is 0.05%. In one embodiment of the formulation administered, pH is 7.6 and bromfenac is 0.05%. In one embodiment of the formulation administered, pH is 7.5 and bromfenac is 0.05%. In one embodiment of the formulation administered, pH is 7.4 and bromfenac is 0.05%. In one embodiment of the formulation administered, pH is 7.3 and bromfenac is 0.05%. In one embodiment of the formulation administered, pH is 7.2 and bromfenac is 0.05%. In one embodiment of the formulation administered, pH is 7.1 and bromfenac is 0.05%. In one embodiment of the formulation administered, pH is 7.0 and bromfenac is 0.05%. In one embodiment of the formulation administered, pH is 6.9 and bromfenac is 0.05%. In one embodiment of the formulation administered, pH is 6.8 and bromfenac is 0.05%. In one embodiment of the formulation administered, pH is 6.7 and bromfenac is 0.05%. In one embodiment of the formulation administered, pH is 6.6 and bromfenac is 0.05%. In one embodiment of the formulation administered, pH is 6.5 and bromfenac is 0.05%. In one embodiment of the formulation administered, pH is 6.4 and bromfenac is 0.05%. In one embodiment of the formulation administered, pH is 6.3 and bromfenac is 0.05%. In one embodiment of the formulation administered, pH is 6.2 and bromfenac is 0.05%. In one embodiment of the formulation administered, pH is 6.1 and bromfenac is 0.05%. In one embodiment of the formulation administered, pH is 6.0 and bromfenac is 0.05%.

In one embodiment of the formulation administered, pH is 8.2 and bromfenac is 0.06%. In one embodiment of the formulation administered, pH is 8.1 and bromfenac is 0.06%. In one embodiment of the formulation administered, pH is 8.0 and bromfenac is 0.06%. In one embodiment of the formulation administered, pH is 7.9 and bromfenac is 0.06%. In one embodiment of the formulation administered, pH is 7.8 and bromfenac is 0.06%. In one embodiment of the formulation administered, pH is 7.7 and bromfenac is 0.06%. In one embodiment of the formulation administered, pH is 7.6 and bromfenac is 0.06%. In one embodiment of the formulation administered, pH is 7.5 and bromfenac is 0.06%. In one embodiment of the formulation administered, pH is 7.4 and bromfenac is 0.06%. In one embodiment of the formulation administered, pH is 7.3 and bromfenac is 0.06%. In one embodiment of the formulation administered, pH is 7.2 and bromfenac is 0.06%. In one embodiment of the formulation administered, pH is 7.1 and bromfenac is 0.06%. In one embodiment of the formulation administered, pH is 7.0 and bromfenac is 0.06%. In one embodiment of the formulation administered, pH is 6.9 and bromfenac is 0.06%. In one embodiment of the formulation administered, pH is 6.8 and bromfenac is 0.06%. In one embodiment of the formulation administered, pH is 6.7 and bromfenac is 0.06%. In one embodiment of the formulation administered, pH is 6.6 and bromfenac is 0.06%. In one embodiment of the formulation administered, pH is 6.5 and bromfenac is 0.06%. In one embodiment of the formulation administered, pH is 6.4 and bromfenac is 0.06%. In one embodiment of the formulation administered, pH is 6.3 and bromfenac is 0.06%. In one embodiment of the formulation administered, pH is 6.2 and bromfenac is 0.06%. In one embodiment of the formulation administered, pH is 6.1 and bromfenac is 0.06%. In one embodiment of the formulation administered, pH is 6.0 and bromfenac is 0.06%.

In one embodiment of the formulation administered, pH is 8.2 and bromfenac is 0.07%. In one embodiment of the formulation administered, pH is 8.1 and bromfenac is 0.07%. In one embodiment of the formulation administered, pH is 8.0 and bromfenac is 0.07%. In one embodiment of the formulation administered, pH is 7.9 and bromfenac is 0.07%. In one embodiment of the formulation administered, pH is 7.8 and bromfenac is 0.07%. In one embodiment of the formulation administered, pH is 7.7 and bromfenac is 0.07%. In one embodiment of the formulation administered, pH is 7.6 and bromfenac is 0.07%. In one embodiment of the formulation administered, pH is 7.5 and bromfenac is 0.07%. In one embodiment of the formulation administered, pH is 7.4 and bromfenac is 0.07%. In one embodiment of the formulation administered, pH is 7.3 and bromfenac is 0.07%. In one embodiment of the formulation administered, pH is 7.2 and bromfenac is 0.07%. In one embodiment of the formulation administered, pH is 7.1 and bromfenac is 0.07%. In one embodiment of the formulation administered, pH is 7.0 and bromfenac is 0.07%. In one embodiment of the formulation administered, pH is 6.9 and bromfenac is 0.07%. In one embodiment of the formulation administered, pH is 6.8 and bromfenac is 0.07%. In one embodiment of the formulation administered, pH is 6.7 and bromfenac is 0.07%. In one embodiment of the formulation administered, pH is 6.6 and bromfenac is 0.07%. In one embodiment of the formulation administered, pH is 6.5 and bromfenac is 0.07%. In one embodiment of the formulation administered, pH is 6.4 and bromfenac is 0.07%. In one embodiment of the formulation administered, pH is 6.3 and bromfenac is 0.07%. In one embodiment of the formulation administered, pH is 6.2 and bromfenac is 0.07%. In one embodiment of the formulation administered, pH is 6.1 and bromfenac is 0.07%. In one embodiment of the formulation administered, pH is 6.0 and bromfenac is 0.07%.

In one embodiment of the formulation administered, pH is 8.2 and bromfenac is 0.08%. In one embodiment of the formulation administered, pH is 8.1 and bromfenac is 0.08%. In one embodiment of the formulation administered, pH is 8.0 and bromfenac is 0.08%. In one embodiment of the formulation administered, pH is 7.9 and bromfenac is 0.08%. In one embodiment of the formulation administered, pH is 7.8 and bromfenac is 0.08%. In one embodiment of the formulation administered, pH is 7.7 and bromfenac is 0.08%. In one embodiment of the formulation administered, pH is 7.6 and bromfenac is 0.08%. In one embodiment of the formulation administered, pH is 7.5 and bromfenac is 0.08%. In one embodiment of the formulation administered, pH is 7.4 and bromfenac is 0.08%. In one embodiment of the formulation administered, pH is 7.3 and bromfenac is 0.08%. In one embodiment of the formulation administered, pH is 7.2 and bromfenac is 0.08%. In one embodiment of the formulation administered, pH is 7.1 and bromfenac is 0.08%. In one embodiment of the formulation administered, pH is 7.0 and bromfenac is 0.08%. In one embodiment of the formulation administered, pH is 6.9 and bromfenac is 0.08%. In one embodiment of the formulation administered, pH is 6.8 and bromfenac is 0.08%. In one embodiment of the formulation administered, pH is 6.7 and bromfenac is 0.08%. In one embodiment of the formulation administered, pH is 6.6 and bromfenac is 0.08%. In one embodiment of the formulation administered, pH is 6.5 and bromfenac is 0.08%. In one embodiment of the formulation administered, pH is 6.4 and bromfenac is 0.08%. In one embodiment of the formulation administered, pH is 6.3 and bromfenac is 0.08%. In one embodiment of the formulation administered, pH is 6.2 and bromfenac is 0.08%. In one embodiment of the formulation administered, pH is 6.1 and bromfenac is 0.08%. In one embodiment of the formulation administered, pH is 6.0 and bromfenac is 0.08%.

In one embodiment of the formulation administered, pH is 8.2 and bromfenac is 0.09%. In one embodiment of the formulation administered, pH is 8.1 and bromfenac is 0.09%. In one embodiment of the formulation administered, pH is 8.0 and bromfenac is 0.09%. In one embodiment of the formulation administered, pH is 7.9 and bromfenac is 0.09%. In one embodiment of the formulation administered, pH is 7.8 and bromfenac is 0.09%. In one embodiment of the formulation administered, pH is 7.7 and bromfenac is 0.09%. In one embodiment of the formulation administered, pH is 7.6 and bromfenac is 0.09%. In one embodiment of the formulation administered, pH is 7.5 and bromfenac is 0.09%. In one embodiment of the formulation administered, pH is 7.4 and bromfenac is 0.09%. In one embodiment of the formulation administered, pH is 7.3 and bromfenac is 0.09%. In one embodiment of the formulation administered, pH is 7.2 and bromfenac is 0.09%. In one embodiment of the formulation administered, pH is 7.1 and bromfenac is 0.09%. In one embodiment of the formulation administered, pH is 7.0 and bromfenac is 0.09%. In one embodiment of the formulation administered, pH is 6.9 and bromfenac is 0.09%. In one embodiment of the formulation administered, pH is 6.8 and bromfenac is 0.09%. In one embodiment of the formulation administered, pH is 6.7 and bromfenac is 0.09%. In one embodiment of the formulation administered, pH is 6.6 and bromfenac is 0.09%. In one embodiment of the formulation administered, pH is 6.5 and bromfenac is 0.09%. In one embodiment of the formulation administered, pH is 6.4 and bromfenac is 0.09%. In one embodiment of the formulation administered, pH is 6.3 and bromfenac is 0.09%. In one embodiment of the formulation administered, pH is 6.2 and bromfenac is 0.09%. In one embodiment of the formulation administered, pH is 6.1 and bromfenac is 0.09%. In one embodiment of the formulation administered, pH is 6.0 and bromfenac is 0.09%.

In one embodiment of the formulation administered, pH is 8.2 and bromfenac is 0.10%. In one embodiment of the formulation administered, pH is 8.1 and bromfenac is 0.10%. In one embodiment of the formulation administered, pH is 8.0 and bromfenac is 0.10%. In one embodiment of the formulation administered, pH is 7.9 and bromfenac is 0.10%. In one embodiment of the formulation administered, pH is 7.8 and bromfenac is 0.10%. In one embodiment of the formulation administered, pH is 7.7 and bromfenac is 0.10%. In one embodiment of the formulation administered, pH is 7.6 and bromfenac is 0.10%. In one embodiment of the formulation administered, pH is 7.5 and bromfenac is 0.10%. In one embodiment of the formulation administered, pH is 7.4 and bromfenac is 0.10%. In one embodiment of the formulation administered, pH is 7.3 and bromfenac is 0.10%. In one embodiment of the formulation administered, pH is 7.2 and bromfenac is 0.10%. In one embodiment of the formulation administered, pH is 7.1 and bromfenac is 0.10%. In one embodiment of the formulation administered, pH is 7.0 and bromfenac is 0.10%. In one embodiment of the formulation administered, pH is 6.9 and bromfenac is 0.10%. In one embodiment of the formulation administered, pH is 6.8 and bromfenac is 0.10%. In one embodiment of the formulation administered, pH is 6.7 and bromfenac is 0.10%. In one embodiment of the formulation administered, pH is 6.6 and bromfenac is 0.10%. In one embodiment of the formulation administered, pH is 6.5 and bromfenac is 0.10%. In one embodiment of the formulation administered, pH is 6.4 and bromfenac is 0.10%. In one embodiment of the formulation administered, pH is 6.3 and bromfenac is 0.10%. In one embodiment of the formulation administered, pH is 6.2 and bromfenac is 0.10%. In one embodiment of the formulation administered, pH is 6.1 and bromfenac is 0.10%. In one embodiment of the formulation administered, pH is 6.0 and bromfenac is 0.10%.

In one embodiment of the formulation administered, pH is 8.2 and bromfenac is 0.11%. In one embodiment of the formulation administered, pH is 8.1 and bromfenac is 0.11%. In one embodiment of the formulation administered, pH is 8.0 and bromfenac is 0.11%. In one embodiment of the formulation administered, pH is 7.9 and bromfenac is 0.11%. In one embodiment of the formulation administered, pH is 7.8 and bromfenac is 0.11%. In one embodiment of the formulation administered, pH is 7.7 and bromfenac is 0.11%. In one embodiment of the formulation administered, pH is 7.6 and bromfenac is 0.11%. In one embodiment of the formulation administered, pH is 7.5 and bromfenac is 0.11%. In one embodiment of the formulation administered, pH is 7.4 and bromfenac is 0.11%. In one embodiment of the formulation administered, pH is 7.3 and bromfenac is 0.11%. In one embodiment of the formulation administered, pH is 7.2 and bromfenac is 0.11%. In one embodiment of the formulation administered, pH is 7.1 and bromfenac is 0.11%. In one embodiment of the formulation administered, pH is 7.0 and bromfenac is 0.11%. In one embodiment of the formulation administered, pH is 6.9 and bromfenac is 0.11%. In one embodiment of the formulation administered, pH is 6.8 and bromfenac is 0.11%. In one embodiment of the formulation administered, pH is 6.7 and bromfenac is 0.11%. In one embodiment of the formulation administered, pH is 6.6 and bromfenac is 0.11%. In one embodiment of the formulation administered, pH is 6.5 and bromfenac is 0.11%. In one embodiment of the formulation administered, pH is 6.4 and bromfenac is 0.11%. In one embodiment of the formulation administered, pH is 6.3 and bromfenac is 0.11%. In one embodiment of the formulation administered, pH is 6.2 and bromfenac is 0.11%. In one embodiment of the formulation administered, pH is 6.1 and bromfenac is 0.11%. In one embodiment of the formulation administered, pH is 6.0 and bromfenac is 0.11%.

In one embodiment of the formulation administered, pH is 8.2 and bromfenac is 0.12%. In one embodiment of the formulation administered, pH is 8.1 and bromfenac is 0.12%. In one embodiment of the formulation administered, pH is 8.0 and bromfenac is 0.12%. In one embodiment of the formulation administered, pH is 7.9 and bromfenac is 0.12%. In one embodiment of the formulation administered, pH is 7.8 and bromfenac is 0.12%. In one embodiment of the formulation administered, pH is 7.7 and bromfenac is 0.12%. In one embodiment of the formulation administered, pH is 7.6 and bromfenac is 0.12%. In one embodiment of the formulation administered, pH is 7.5 and bromfenac is 0.12%. In one embodiment of the formulation administered, pH is 7.4 and bromfenac is 0.12%. In one embodiment of the formulation administered, pH is 7.3 and bromfenac is 0.12%. In one embodiment of the formulation administered, pH is 7.2 and bromfenac is 0.12%. In one embodiment of the formulation administered, pH is 7.1 and bromfenac is 0.12%. In one embodiment of the formulation administered, pH is 7.0 and bromfenac is 0.12%. In one embodiment of the formulation administered, pH is 6.9 and bromfenac is 0.12%. In one embodiment of the formulation administered, pH is 6.8 and bromfenac is 0.12%. In one embodiment of the formulation administered, pH is 6.7 and bromfenac is 0.12%. In one embodiment of the formulation administered, pH is 6.6 and bromfenac is 0.12%. In one embodiment of the formulation administered, pH is 6.5 and bromfenac is 0.12%. In one embodiment of the formulation administered, pH is 6.4 and bromfenac is 0.12%. In one embodiment of the formulation administered, pH is 6.3 and bromfenac is 0.12%. In one embodiment of the formulation administered, pH is 6.2 and bromfenac is 0.12%. In one embodiment of the formulation administered, pH is 6.1 and bromfenac is 0.12%. In one embodiment of the formulation administered, pH is 6.0 and bromfenac is 0.12%.

In one embodiment of the formulation administered, pH is 8.2 and bromfenac is 0.13%. In one embodiment of the formulation administered, pH is 8.1 and bromfenac is 0.13%. In one embodiment of the formulation administered, pH is 8.0 and bromfenac is 0.13%. In one embodiment of the formulation administered, pH is 7.9 and bromfenac is 0.13%. In one embodiment of the formulation administered, pH is 7.8 and bromfenac is 0.13%. In one embodiment of the formulation administered, pH is 7.7 and bromfenac is 0.13%. In one embodiment of the formulation administered, pH is 7.6 and bromfenac is 0.13%. In one embodiment of the formulation administered, pH is 7.5 and bromfenac is 0.13%. In one embodiment of the formulation administered, pH is 7.4 and bromfenac is 0.13%. In one embodiment of the formulation administered, pH is 7.3 and bromfenac is 0.13%. In one embodiment of the formulation administered, pH is 7.2 and bromfenac is 0.13%. In one embodiment of the formulation administered, pH is 7.1 and bromfenac is 0.13%. In one embodiment of the formulation administered, pH is 7.0 and bromfenac is 0.13%. In one embodiment of the formulation administered, pH is 6.9 and bromfenac is 0.13%. In one embodiment of the formulation administered, pH is 6.8 and bromfenac is 0.13%. In one embodiment of the formulation administered, pH is 6.7 and bromfenac is 0.13%. In one embodiment of the formulation administered, pH is 6.6 and bromfenac is 0.13%. In one embodiment of the formulation administered, pH is 6.5 and bromfenac is 0.13%. In one embodiment of the formulation administered, pH is 6.4 and bromfenac is 0.13%. In one embodiment of the formulation administered, pH is 6.3 and bromfenac is 0.13%. In one embodiment of the formulation administered, pH is 6.2 and bromfenac is 0.13%. In one embodiment of the formulation administered, pH is 6.1 and bromfenac is 0.13%. In one embodiment of the formulation administered, pH is 6.0 and bromfenac is 0.13%.

In one embodiment of the formulation administered, pH is 8.2 and bromfenac is 0.14%. In one embodiment of the formulation administered, pH is 8.1 and bromfenac is 0.14%. In one embodiment of the formulation administered, pH is 8.0 and bromfenac is 0.14%. In one embodiment of the formulation administered, pH is 7.9 and bromfenac is 0.14%. In one embodiment of the formulation administered, pH is 7.8 and bromfenac is 0.14%. In one embodiment of the formulation administered, pH is 7.7 and bromfenac is 0.14%. In one embodiment of the formulation administered, pH is 7.6 and bromfenac is 0.14%. In one embodiment of the formulation administered, pH is 7.5 and bromfenac is 0.14%. In one embodiment of the formulation administered, pH is 7.4 and bromfenac is 0.14%. In one embodiment of the formulation administered, pH is 7.3 and bromfenac is 0.14%. In one embodiment of the formulation administered, pH is 7.2 and bromfenac is 0.14%. In one embodiment of the formulation administered, pH is 7.1 and bromfenac is 0.14%. In one embodiment of the formulation administered, pH is 7.0 and bromfenac is 0.14%. In one embodiment of the formulation administered, pH is 6.9 and bromfenac is 0.14%. In one embodiment of the formulation administered, pH is 6.8 and bromfenac is 0.14%. In one embodiment of the formulation administered, pH is 6.7 and bromfenac is 0.14%. In one embodiment of the formulation administered, pH is 6.6 and bromfenac is 0.14%. In one embodiment of the formulation administered, pH is 6.5 and bromfenac is 0.14%. In one embodiment of the formulation administered, pH is 6.4 and bromfenac is 0.14%. In one embodiment of the formulation administered, pH is 6.3 and bromfenac is 0.14%. In one embodiment of the formulation administered, pH is 6.2 and bromfenac is 0.14%. In one embodiment of the formulation administered, pH is 6.1 and bromfenac is 0.14%. In one embodiment of the formulation administered, pH is 6.0 and bromfenac is 0.14%.

In one embodiment of the formulation administered, pH is 8.2 and bromfenac is 0.15%. In one embodiment of the formulation administered, pH is 8.1 and bromfenac is 0.15%. In one embodiment of the formulation administered, pH is 8.0 and bromfenac is 0.15%. In one embodiment of the formulation administered, pH is 7.9 and bromfenac is 0.15%. In one embodiment of the formulation administered, pH is 7.8 and bromfenac is 0.15%. In one embodiment of the formulation administered, pH is 7.7 and bromfenac is 0.15%. In one embodiment of the formulation administered, pH is 7.6 and bromfenac is 0.15%. In one embodiment of the formulation administered, pH is 7.5 and bromfenac is 0.15%. In one embodiment of the formulation administered, pH is 7.4 and bromfenac is 0.15%. In one embodiment of the formulation administered, pH is 7.3 and bromfenac is 0.15%. In one embodiment of the formulation administered, pH is 7.2 and bromfenac is 0.15%. In one embodiment of the formulation administered, pH is 7.1 and bromfenac is 0.15%. In one embodiment of the formulation administered, pH is 7.0 and bromfenac is 0.15%. In one embodiment of the formulation administered, pH is 6.9 and bromfenac is 0.15%. In one embodiment of the formulation administered, pH is 6.8 and bromfenac is 0.15%. In one embodiment of the formulation administered, pH is 6.7 and bromfenac is 0.15%. In one embodiment of the formulation administered, pH is 6.6 and bromfenac is 0.15%. In one embodiment of the formulation administered, pH is 6.5 and bromfenac is 0.15%. In one embodiment of the formulation administered, pH is 6.4 and bromfenac is 0.15%. In one embodiment of the formulation administered, pH is 6.3 and bromfenac is 0.15%. In one embodiment of the formulation administered, pH is 6.2 and bromfenac is 0.15%. In one embodiment of the formulation administered, pH is 6.1 and bromfenac is 0.15%. In one embodiment of the formulation administered, pH is 6.0 and bromfenac is 0.15%.

In one embodiment of the formulation administered, pH is 8.2 and bromfenac is 0.16%. In one embodiment of the formulation administered, pH is 8.1 and bromfenac is 0.16%. In one embodiment of the formulation administered, pH is 8.0 and bromfenac is 0.16%. In one embodiment of the formulation administered, pH is 7.9 and bromfenac is 0.16%. In one embodiment of the formulation administered, pH is 7.8 and bromfenac is 0.16%. In one embodiment of the formulation administered, pH is 7.7 and bromfenac is 0.16%. In one embodiment of the formulation administered, pH is 7.6 and bromfenac is 0.16%. In one embodiment of the formulation administered, pH is 7.5 and bromfenac is 0.16%. In one embodiment of the formulation administered, pH is 7.4 and bromfenac is 0.16%. In one embodiment of the formulation administered, pH is 7.3 and bromfenac is 0.16%. In one embodiment of the formulation administered, pH is 7.2 and bromfenac is 0.16%. In one embodiment of the formulation administered, pH is 7.1 and bromfenac is 0.16%. In one embodiment of the formulation administered, pH is 7.0 and bromfenac is 0.16%. In one embodiment of the formulation administered, pH is 6.9 and bromfenac is 0.16%. In one embodiment of the formulation administered, pH is 6.8 and bromfenac is 0.16%. In one embodiment of the formulation administered, pH is 6.7 and bromfenac is 0.16%. In one embodiment of the formulation administered, pH is 6.6 and bromfenac is 0.16%. In one embodiment of the formulation administered, pH is 6.5 and bromfenac is 0.16%. In one embodiment of the formulation administered, pH is 6.4 and bromfenac is 0.16%. In one embodiment of the formulation administered, pH is 6.3 and bromfenac is 0.16%. In one embodiment of the formulation administered, pH is 6.2 and bromfenac is 0.16%. In one embodiment of the formulation administered, pH is 6.1 and bromfenac is 0.16%. In one embodiment of the formulation administered, pH is 6.0 and bromfenac is 0.16%.

In one embodiment of the formulation administered, pH is 8.2 and bromfenac is 0.17%. In one embodiment of the formulation administered, pH is 8.1 and bromfenac is 0.17%. In one embodiment of the formulation administered, pH is 8.0 and bromfenac is 0.17%. In one embodiment of the formulation administered, pH is 7.9 and bromfenac is 0.17%. In one embodiment of the formulation administered, pH is 7.8 and bromfenac is 0.17%. In one embodiment of the formulation administered, pH is 7.7 and bromfenac is 0.17%. In one embodiment of the formulation administered, pH is 7.6 and bromfenac is 0.17%. In one embodiment of the formulation administered, pH is 7.5 and bromfenac is 0.17%. In one embodiment of the formulation administered, pH is 7.4 and bromfenac is 0.17%. In one embodiment of the formulation administered, pH is 7.3 and bromfenac is 0.17%. In one embodiment of the formulation administered, pH is 7.2 and bromfenac is 0.17%. In one embodiment of the formulation administered, pH is 7.1 and bromfenac is 0.17%. In one embodiment of the formulation administered, pH is 7.0 and bromfenac is 0.17%. In one embodiment of the formulation administered, pH is 6.9 and bromfenac is 0.17%. In one embodiment of the formulation administered, pH is 6.8 and bromfenac is 0.17%. In one embodiment of the formulation administered, pH is 6.7 and bromfenac is 0.17%. In one embodiment of the formulation administered, pH is 6.6 and bromfenac is 0.17%. In one embodiment of the formulation administered, pH is 6.5 and bromfenac is 0.17%. In one embodiment of the formulation administered, pH is 6.4 and bromfenac is 0.17%. In one embodiment of the formulation administered, pH is 6.3 and bromfenac is 0.17%. In one embodiment of the formulation administered, pH is 6.2 and bromfenac is 0.17%. In one embodiment of the formulation administered, pH is 6.1 and bromfenac is 0.17%. In one embodiment of the formulation administered, pH is 6.0 and bromfenac is 0.17%.

In one embodiment of the formulation administered, pH is 8.2 and bromfenac is 0.18%. In one embodiment of the formulation administered, pH is 8.1 and bromfenac is 0.18%. In one embodiment of the formulation administered, pH is 8.0 and bromfenac is 0.18%. In one embodiment of the formulation administered, pH is 7.9 and bromfenac is 0.18%. In one embodiment of the formulation administered, pH is 7.8 and bromfenac is 0.18%. In one embodiment of the formulation administered, pH is 7.7 and bromfenac is 0.18%. In one embodiment of the formulation administered, pH is 7.6 and bromfenac is 0.18%. In one embodiment of the formulation administered, pH is 7.5 and bromfenac is 0.18%. In one embodiment of the formulation administered, pH is 7.4 and bromfenac is 0.18%. In one embodiment of the formulation administered, pH is 7.3 and bromfenac is 0.18%. In one embodiment of the formulation administered, pH is 7.2 and bromfenac is 0.18%. In one embodiment of the formulation administered, pH is 7.1 and bromfenac is 0.18%. In one embodiment of the formulation administered, pH is 7.0 and bromfenac is 0.18%. In one embodiment of the formulation administered, pH is 6.9 and bromfenac is 0.18%. In one embodiment of the formulation administered, pH is 6.8 and bromfenac is 0.18%. In one embodiment of the formulation administered, pH is 6.7 and bromfenac is 0.18%. In one embodiment of the formulation administered, pH is 6.6 and bromfenac is 0.18%. In one embodiment of the formulation administered, pH is 6.5 and bromfenac is 0.18%. In one embodiment of the formulation administered, pH is 6.4 and bromfenac is 0.18%. In one embodiment of the formulation administered, pH is 6.3 and bromfenac is 0.18%. In one embodiment of the formulation administered, pH is 6.2 and bromfenac is 0.18%. In one embodiment of the formulation administered, pH is 6.1 and bromfenac is 0.18%. In one embodiment of the formulation administered, pH is 6.0 and bromfenac is 0.18%.

In one embodiment of the formulation administered, pH is 8.2 and bromfenac is 0.19%. In one embodiment of the formulation administered, pH is 8.1 and bromfenac is 0.19%. In one embodiment of the formulation administered, pH is 8.0 and bromfenac is 0.19%. In one embodiment of the formulation administered, pH is 7.9 and bromfenac is 0.19%. In one embodiment of the formulation administered, pH is 7.8 and bromfenac is 0.19%. In one embodiment of the formulation administered, pH is 7.7 and bromfenac is 0.19%. In one embodiment of the formulation administered, pH is 7.6 and bromfenac is 0.19%. In one embodiment of the formulation administered, pH is 7.5 and bromfenac is 0.19%. In one embodiment of the formulation administered, pH is 7.4 and bromfenac is 0.19%. In one embodiment of the formulation administered, pH is 7.3 and bromfenac is 0.19%. In one embodiment of the formulation administered, pH is 7.2 and bromfenac is 0.19%. In one embodiment of the formulation administered, pH is 7.1 and bromfenac is 0.19%. In one embodiment of the formulation administered, pH is 7.0 and bromfenac is 0.19%. In one embodiment of the formulation administered, pH is 6.9 and bromfenac is 0.19%. In one embodiment of the formulation administered, pH is 6.8 and bromfenac is 0.19%. In one embodiment of the formulation administered, pH is 6.7 and bromfenac is 0.19%. In one embodiment of the formulation administered, pH is 6.6 and bromfenac is 0.19%. In one embodiment of the formulation administered, pH is 6.5 and bromfenac is 0.19%. In one embodiment of the formulation administered, pH is 6.4 and bromfenac is 0.19%. In one embodiment of the formulation administered, pH is 6.3 and bromfenac is 0.19%. In one embodiment of the formulation administered, pH is 6.2 and bromfenac is 0.19%. In one embodiment of the formulation administered, pH is 6.1 and bromfenac is 0.19%. In one embodiment of the formulation administered, pH is 6.0 and bromfenac is 0.19%.

In one embodiment of the formulation administered, pH is 8.2 and bromfenac is 0.20%. In one embodiment of the formulation administered, pH is 8.1 and bromfenac is 0.20%. In one embodiment of the formulation administered, pH is 8.0 and bromfenac is 0.20%. In one embodiment of the formulation administered, pH is 7.9 and bromfenac is 0.20%. In one embodiment of the formulation administered, pH is 7.8 and bromfenac is 0.20%. In one embodiment of the formulation administered, pH is 7.7 and bromfenac is 0.20%. In one embodiment of the formulation administered, pH is 7.6 and bromfenac is 0.20%. In one embodiment of the formulation administered, pH is 7.5 and bromfenac is 0.20%. In one embodiment of the formulation administered, pH is 7.4 and bromfenac is 0.20%. In one embodiment of the formulation administered, pH is 7.3 and bromfenac is 0.20%. In one embodiment of the formulation administered, pH is 7.2 and bromfenac is 0.20%. In one embodiment of the formulation administered, pH is 7.1 and bromfenac is 0.20%. In one embodiment of the formulation administered, pH is 7.0 and bromfenac is 0.20%. In one embodiment of the formulation administered, pH is 6.9 and bromfenac is 0.20%. In one embodiment of the formulation administered, pH is 6.8 and bromfenac is 0.20%. In one embodiment of the formulation administered, pH is 6.7 and bromfenac is 0.20%. In one embodiment of the formulation administered, pH is 6.6 and bromfenac is 0.20%. In one embodiment of the formulation administered, pH is 6.5 and bromfenac is 0.20%. In one embodiment of the formulation administered, pH is 6.4 and bromfenac is 0.20%. In one embodiment of the formulation administered, pH is 6.3 and bromfenac is 0.20%. In one embodiment of the formulation administered, pH is 6.2 and bromfenac is 0.20%. In one embodiment of the formulation administered, pH is 6.1 and bromfenac is 0.20%. In one embodiment of the formulation administered, pH is 6.0 and bromfenac is 0.20%.

Three formulation series were administered to rabbits in pharmacokinetic studies. In one series of formulations, bromfenac was 0.18% and pH was varied from pH 7.0 to pH 8.3. In another formulation series, bromfenac was 0.09% and pH varied from pH 7.0 to pH 8.3. In another formulation series, bromfenac was 0.07% and pH varied from pH 7.0 to pH 8.3. Administration of formulations with bromfenac present at concentrations <0.09% with pH<pH 8.3 resulted in bromfenac levels in target tissues in the front of the eye (iris, ciliary body) that were equal to or greater than levels seen with administration of formulations with bromfenac present at 0.09%. As one example, 0.09% bromfenac solution formulated at pH 8.3 achieved iris and ciliary body bromfenac concentrations of 0.083 ppm in rabbit eyes at 2 hours. As one example, 0.07% bromfenac solution formulated at pH 7.8 achieved iris and ciliary body bromfenac concentrations of 0.110 ppm in rabbit eyes at 2 hours. Administration of a bromfenac solution to a patient at a bromfenac concentration below 0.09% advantageously improved the benefit-to-safety ratio of bromfenac therapy. One skilled in this art considers a formulation for topical ophthalmic administration having a bromfenac concentration less than 0.09% unlikely to result in a sufficient reduction in pain and inflammation when topically administered once-daily to a patient the day before and for 14 days following cataract surgery. This was because the amount of drug reaching the target tissues would be concomitantly reduced.

Figure 1B:
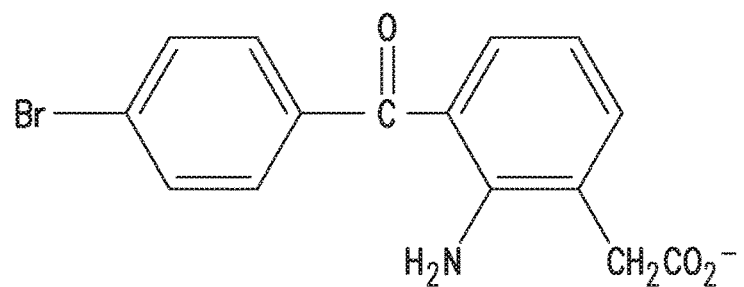
FIG. 1B shows the chemical structure of the carboxylate anion of bromfenac.
Figure 1C:
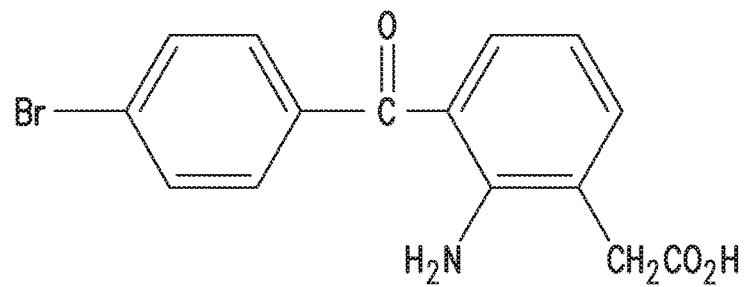
FIG. 1C shows the chemical structure of bromfenac.
Figure 2:
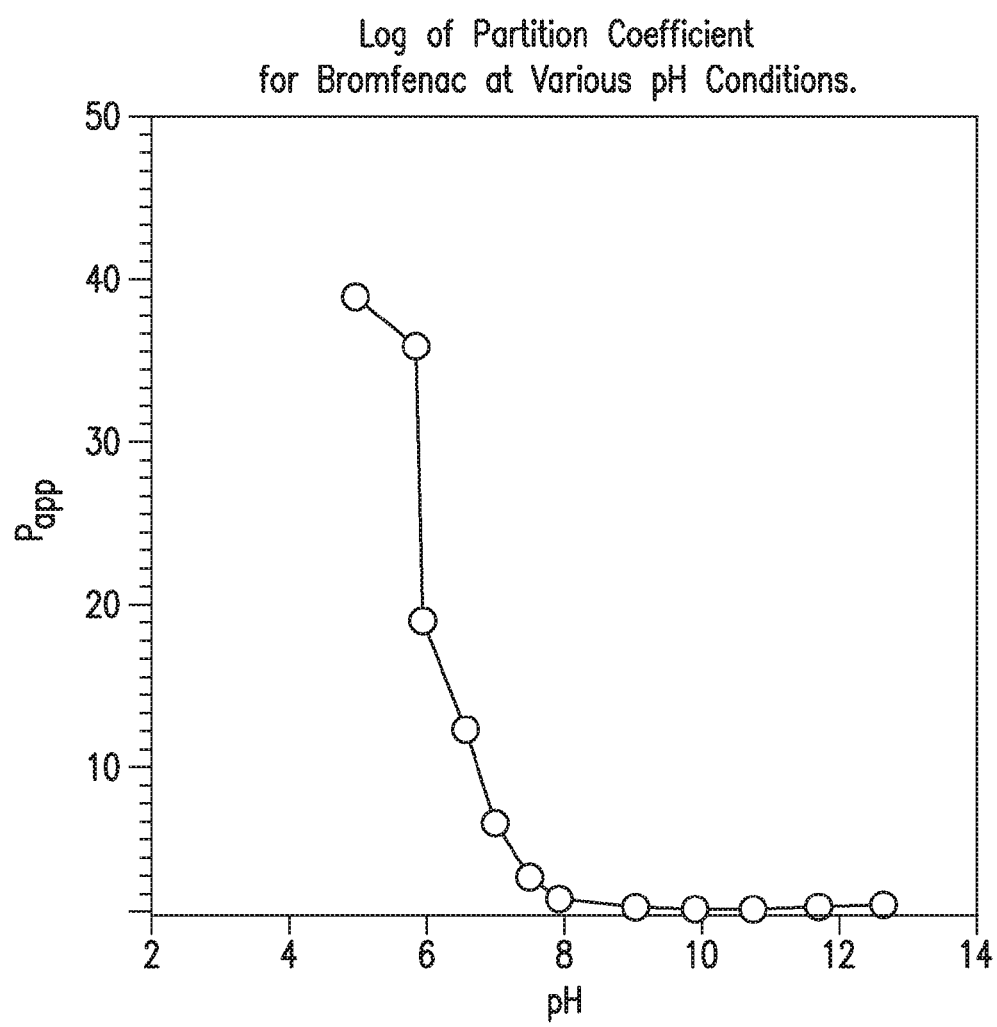
FIG. 2 is a graph of the log of the partition coefficient for bromfenac at various pH conditions.
Figure 3:
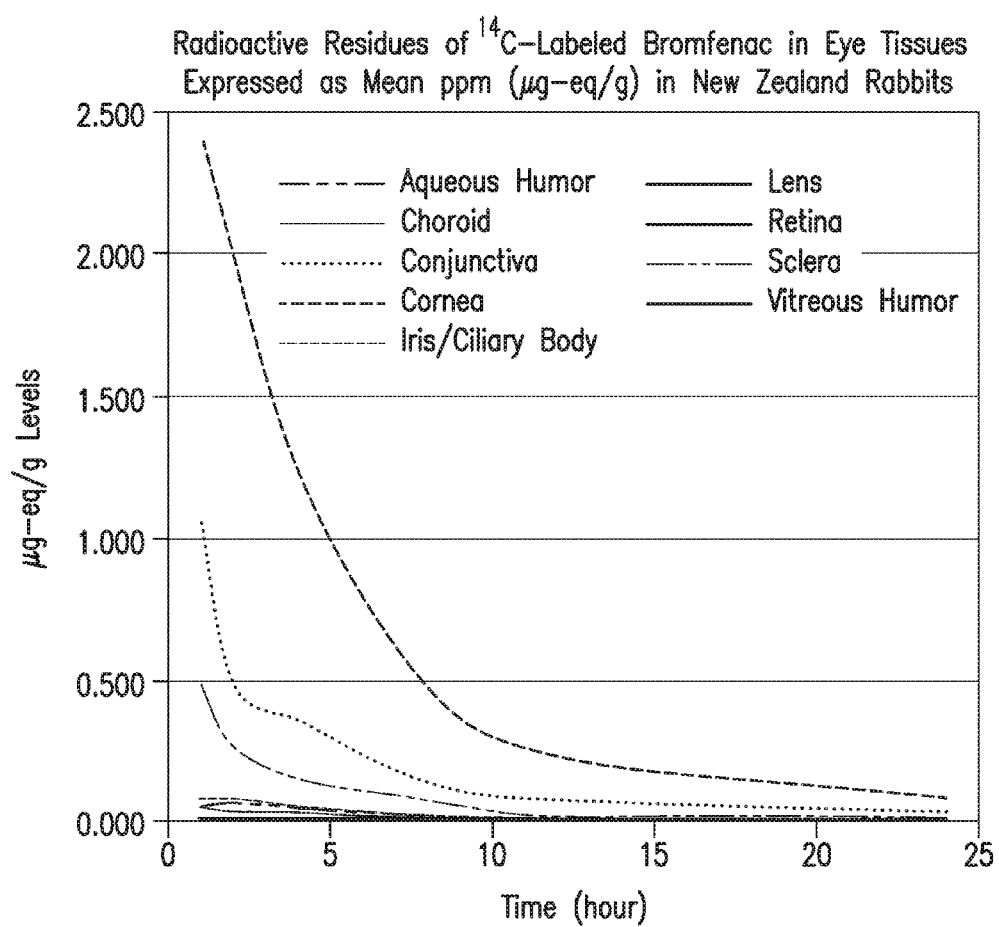
FIG. 3 is a graph of the radioactive residues of $^{14}$C-labeled bromfenac in eye tissues expressed as mean ppm (μg-eq/g) in New Zealand rabbits.
Figure 4:
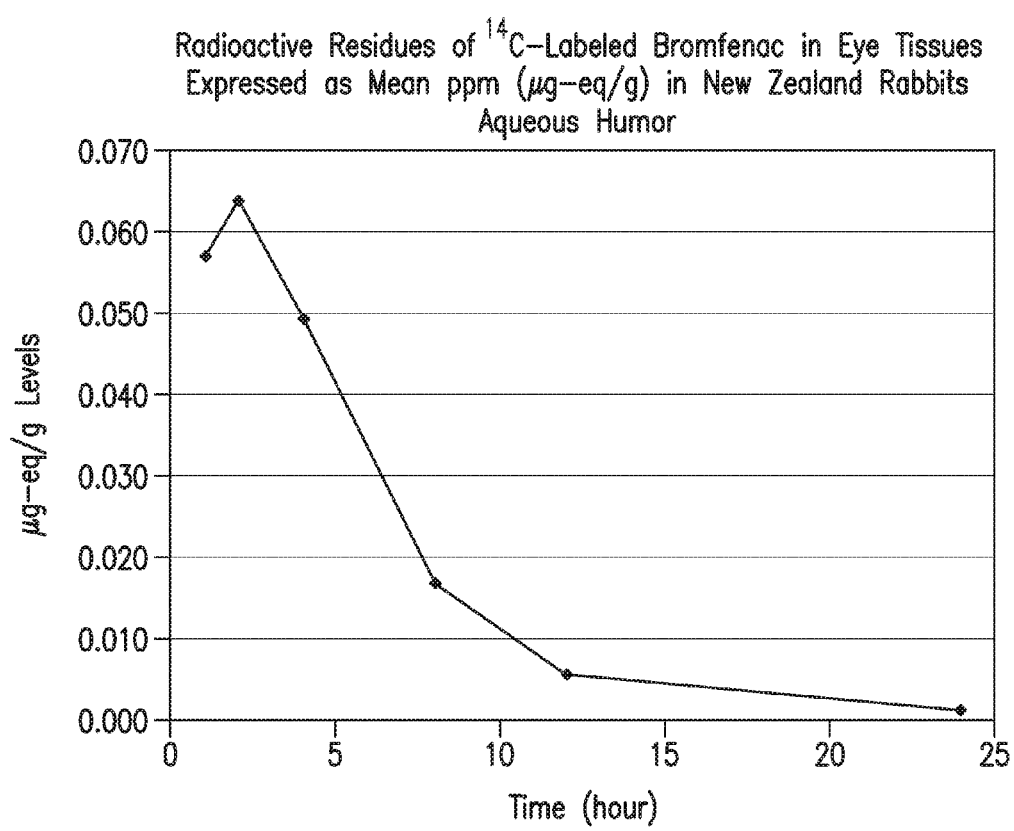
FIG. 4 is a graph of the radioactive residues of $^{14}$C-labeled bromfenac in eye tissues expressed as mean ppm (μg-eq/g) in New Zealand rabbits aqueous humor.
Figure 5:
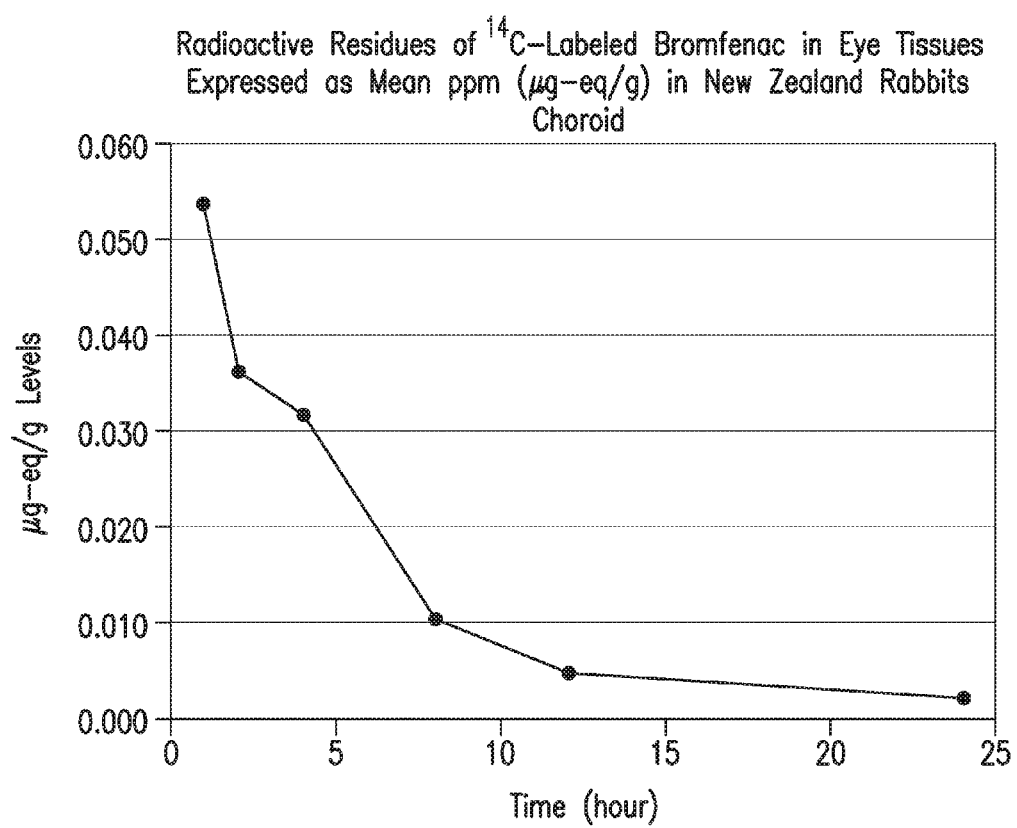
FIG. 5 is a graph of the radioactive residues of $^{14}$C-labeled bromfenac in eye tissues expressed as mean ppm (μg-eq/g) in New Zealand rabbits choroid.
Figure 6:
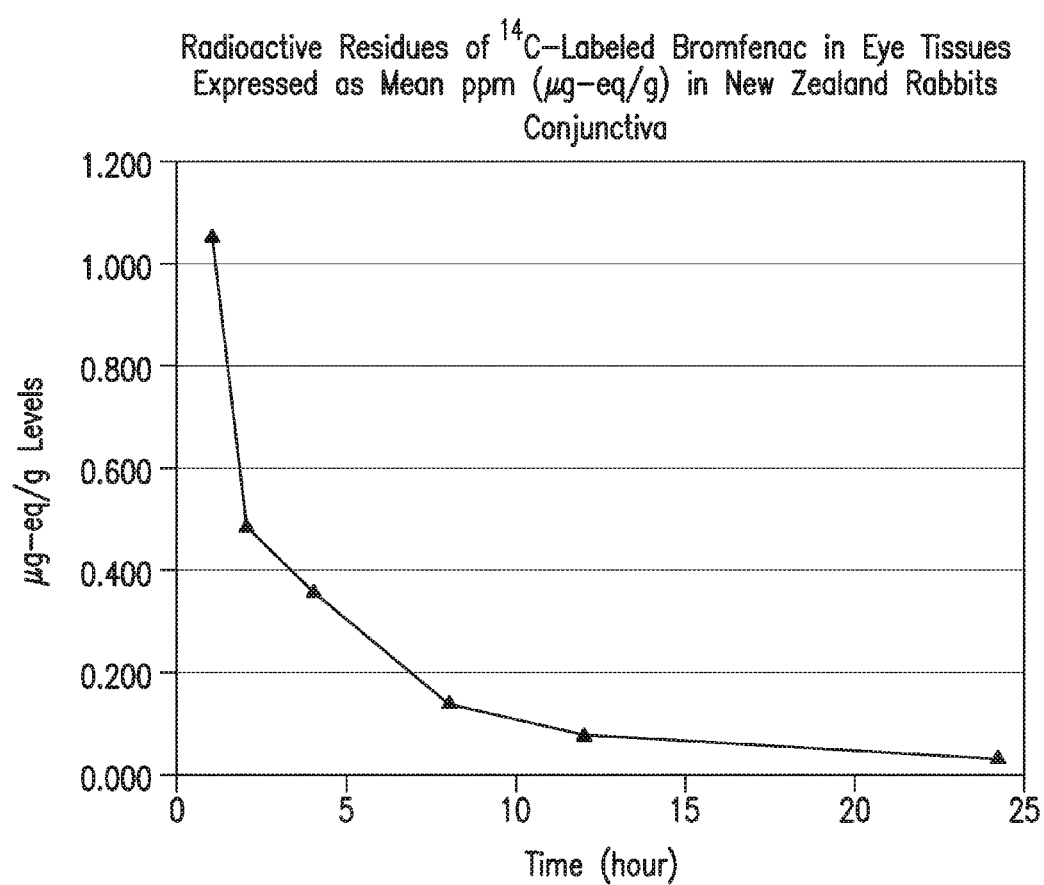
FIG. 6 is a graph of the radioactive residues of $^{14}$C-labeled bromfenac in eye tissues expressed as mean ppm (μg-eq/g) in New Zealand rabbits conjunctiva.
Figure 7:
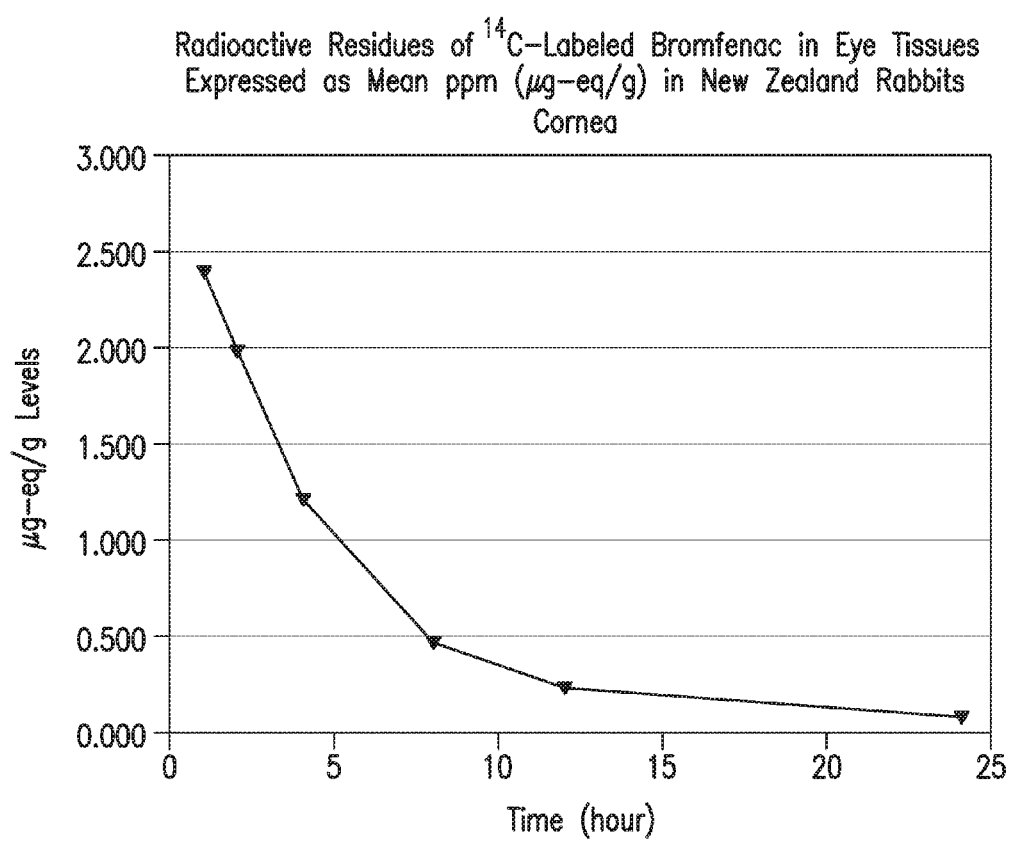
FIG. 7 is a graph of the radioactive residues of $^{14}$C-labeled bromfenac in eye tissues expressed as mean ppm (μg-eq/g) in New Zealand rabbits cornea.
Figure 8:
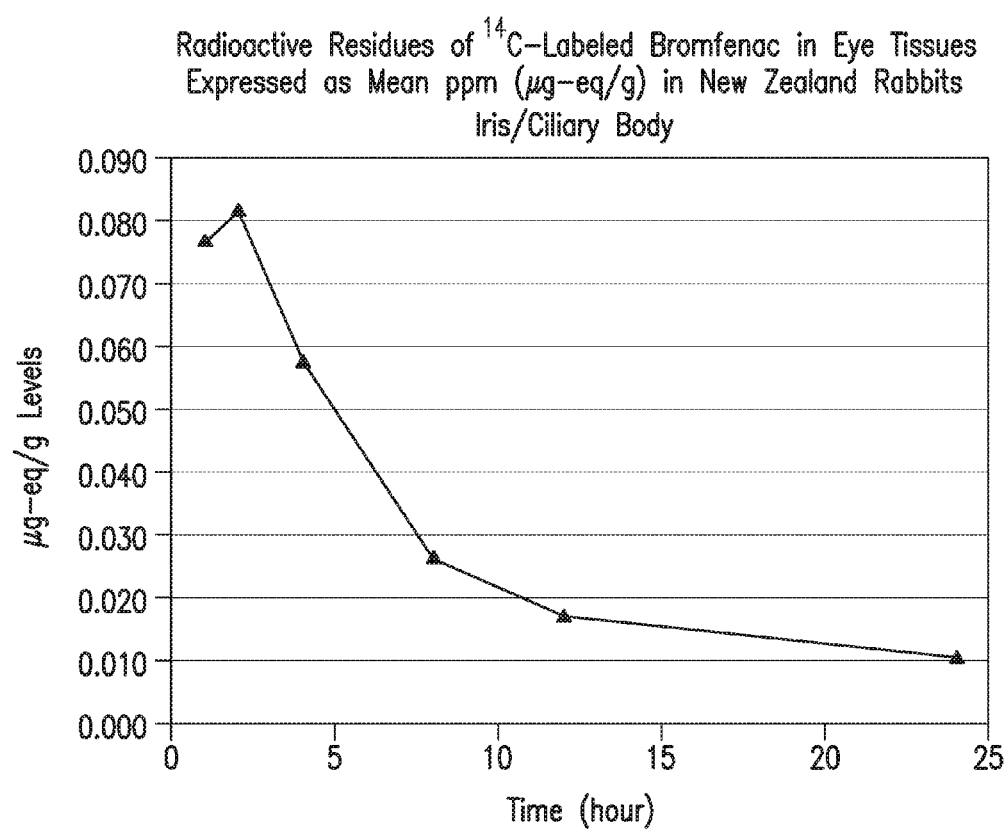
FIG. 8 is a graph of the radioactive residues of $^{14}$C-labeled bromfenac in eye tissues expressed as mean ppm (μg-eq/g) in New Zealand rabbits iris/ciliary body.
Figure 9:
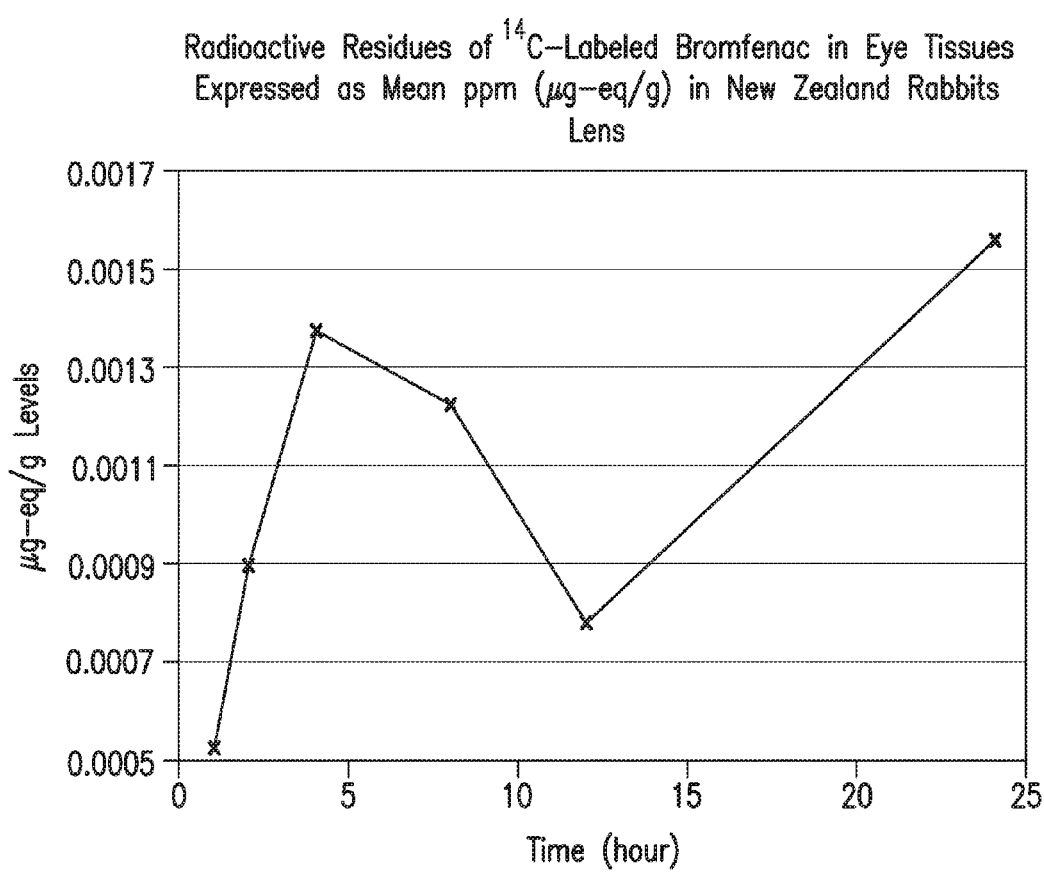
FIG. 9 is a graph of the radioactive residues of $^{14}$C-labeled bromfenac in eye tissues expressed as mean ppm (μg-eq/g) in New Zealand rabbits lens.
Figure 10:
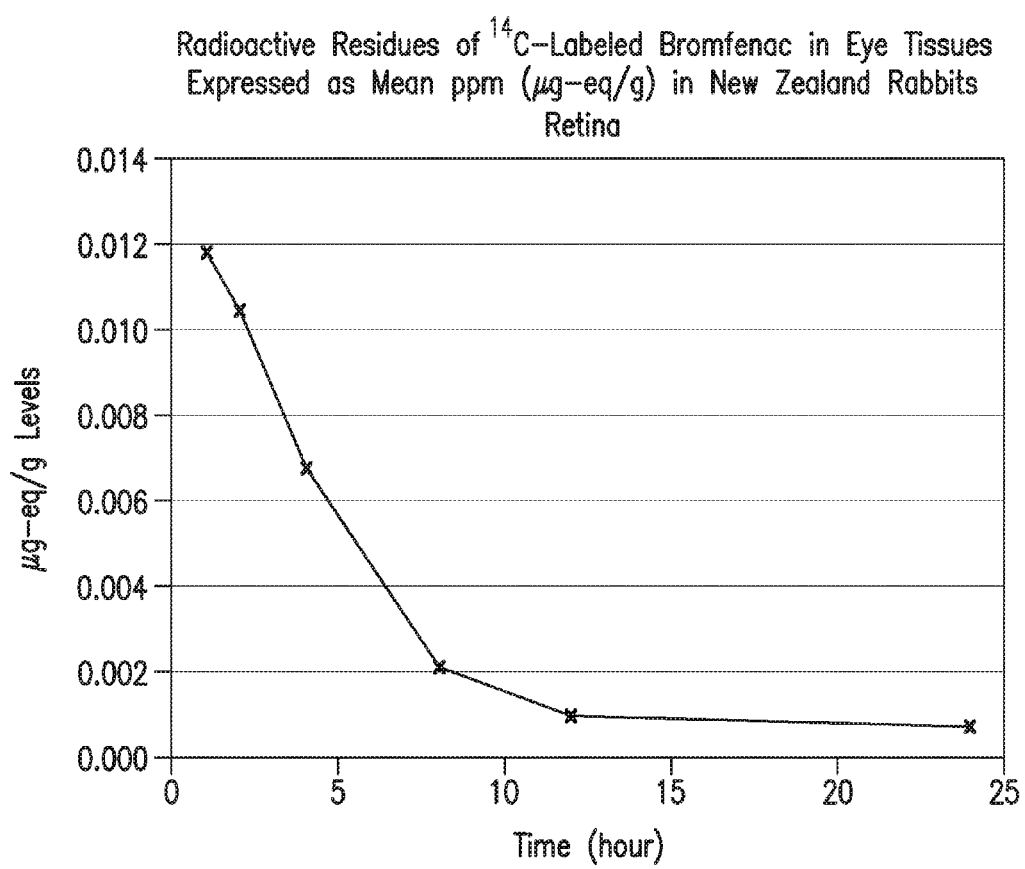
FIG. 10 is a graph of the radioactive residues of $^{14}$C-labeled bromfenac in eye tissues expressed as mean ppm (μg-eq/g) in New Zealand rabbits retina.
Figure 11:
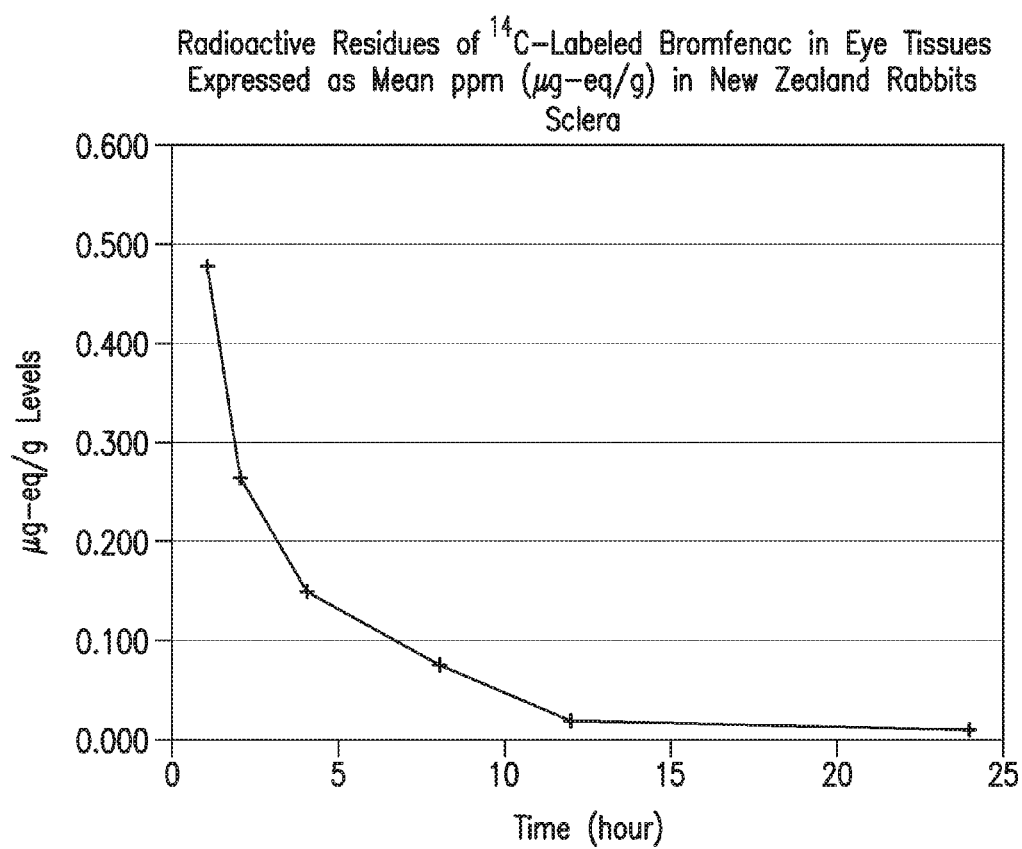
FIG. 11 is a graph of the radioactive residues of $^{14}$C-labeled bromfenac in eye tissues expressed as mean ppm (μg-eq/g) in New Zealand rabbits sclera.
Figure 12:
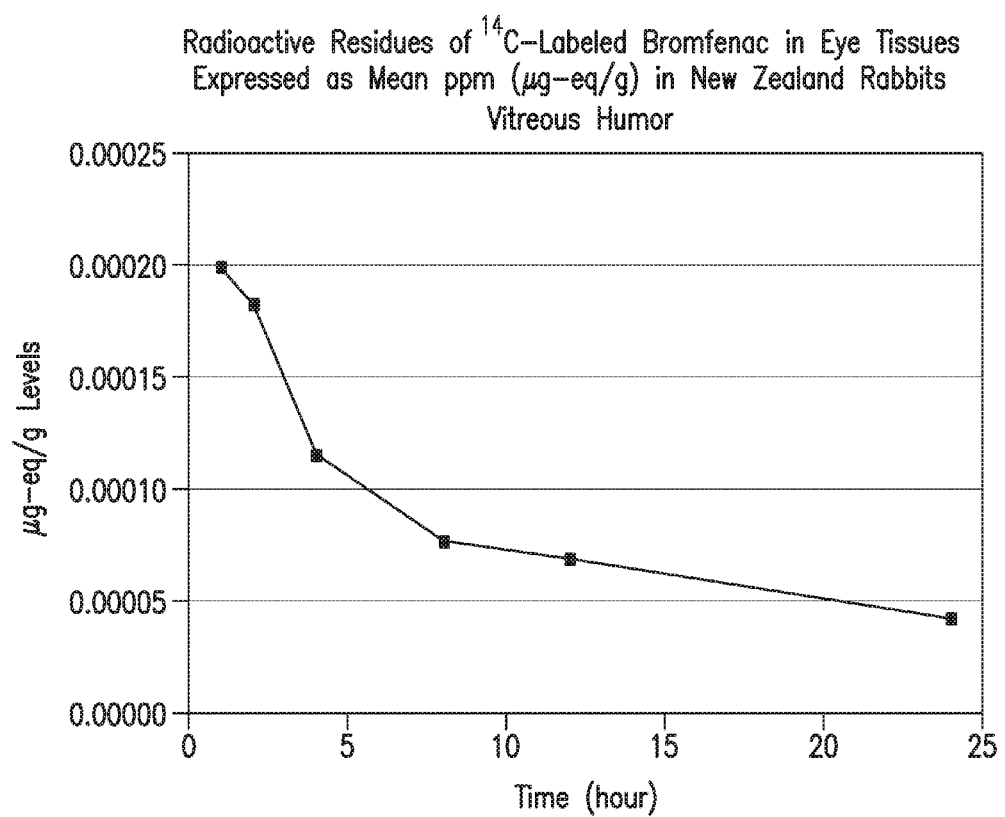
FIG. 12 is a graph of the radioactive residues of $^{14}$C-labeled bromfenac in eye tissues expressed as mean ppm (μg-eq/g) in New Zealand rabbits vitreous humor.
Figure 13:
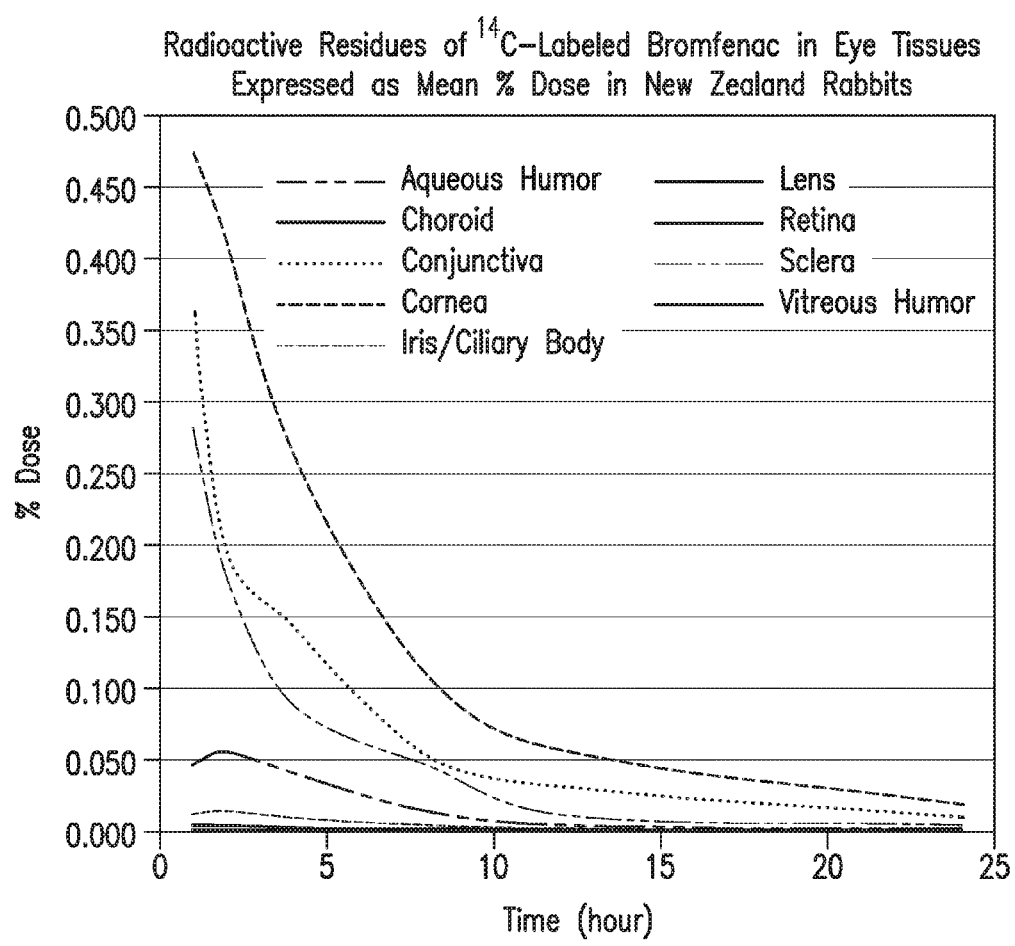
FIG. 13 is a graph of the radioactive residues of $^{14}$C-labeled bromfenac in eye tissues expressed as mean percent dose in New Zealand rabbits.
Figure 14:
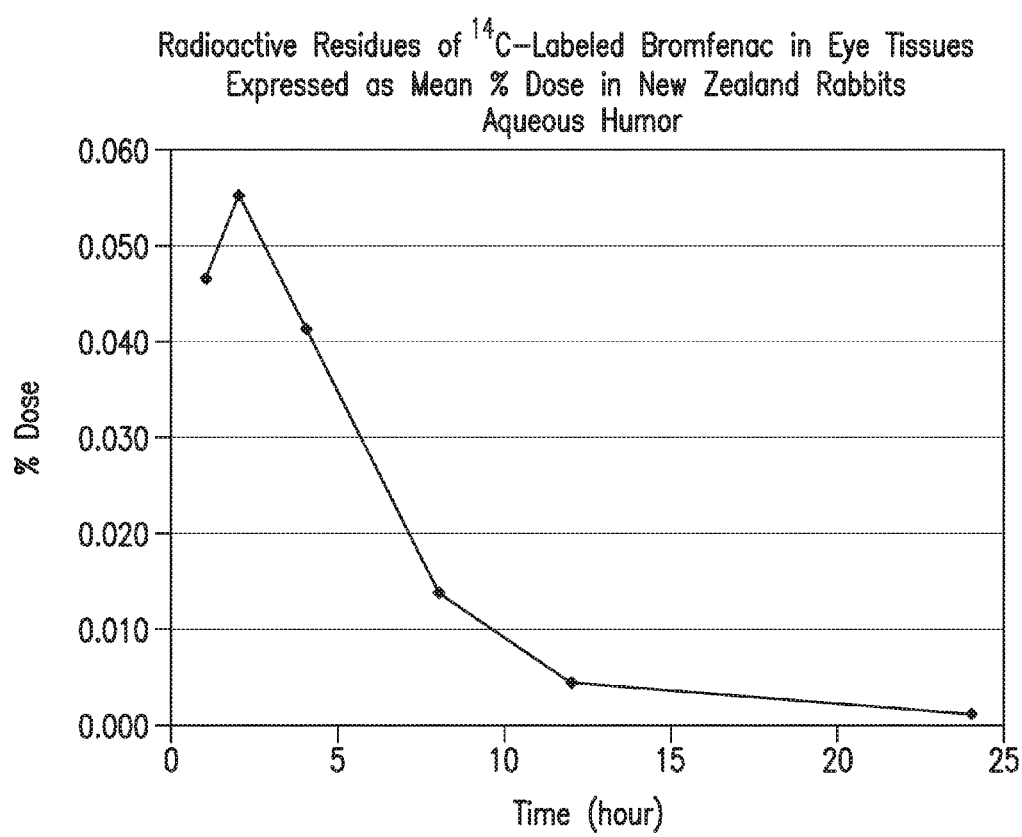
FIG. 14 is a graph of the radioactive residues of $^{14}$C-labeled bromfenac in eye tissues expressed as mean percent dose in New Zealand rabbits aqueous humor.
Figure 15:
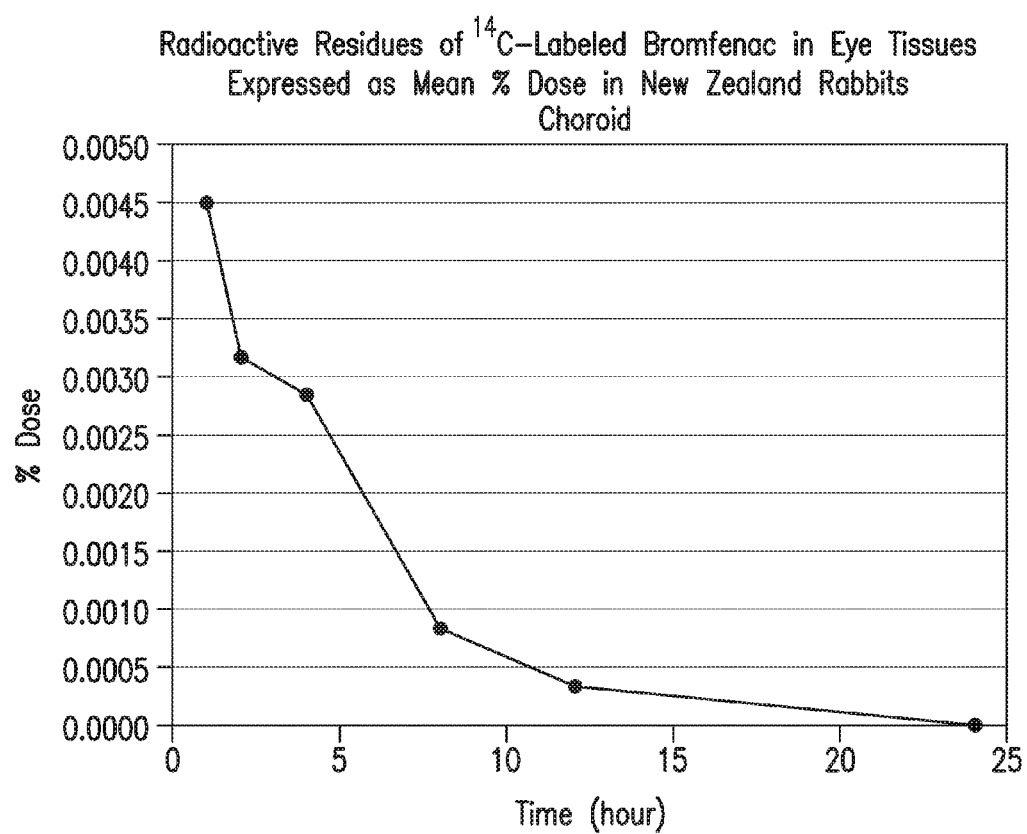
FIG. 15 is a graph of the radioactive residues of $^{14}$C-labeled bromfenac in eye tissues expressed as mean percent dose in New Zealand rabbits choroid.
Figure 16:
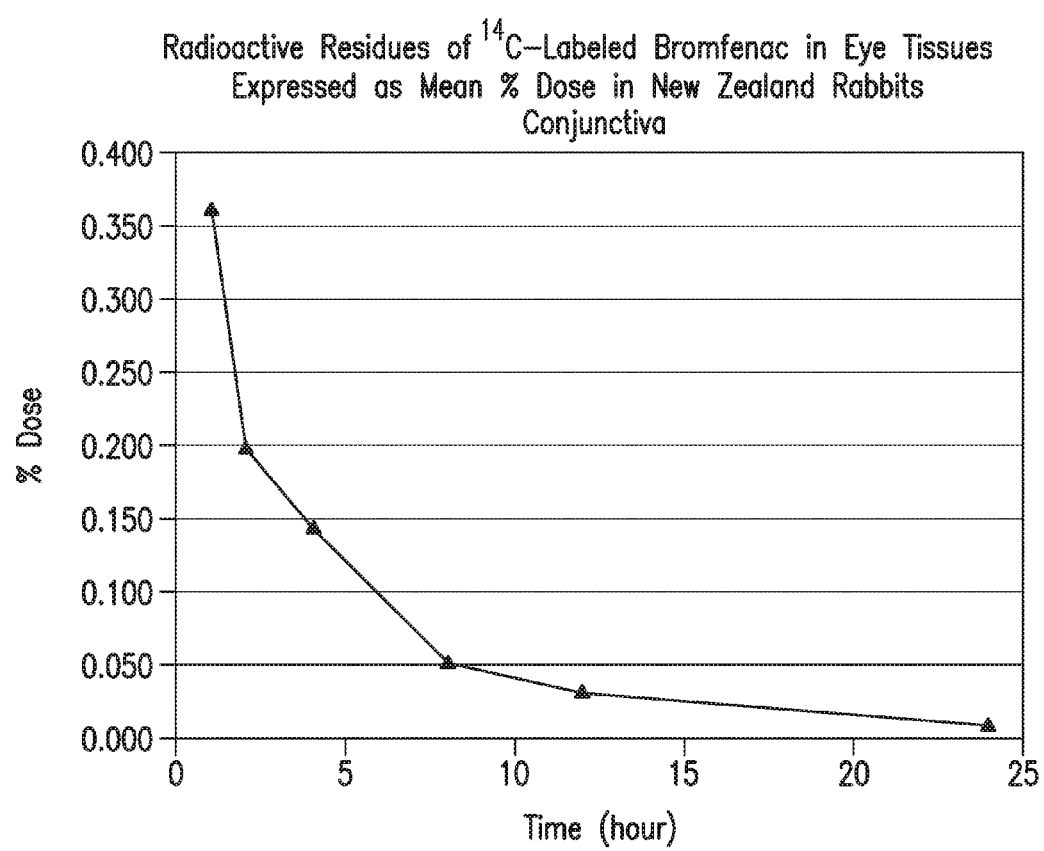
FIG. 16 is a graph of the radioactive residues of $^{14}$C-labeled bromfenac in eye tissues expressed as mean percent dose in New Zealand rabbits conjunctiva.
Figure 17:
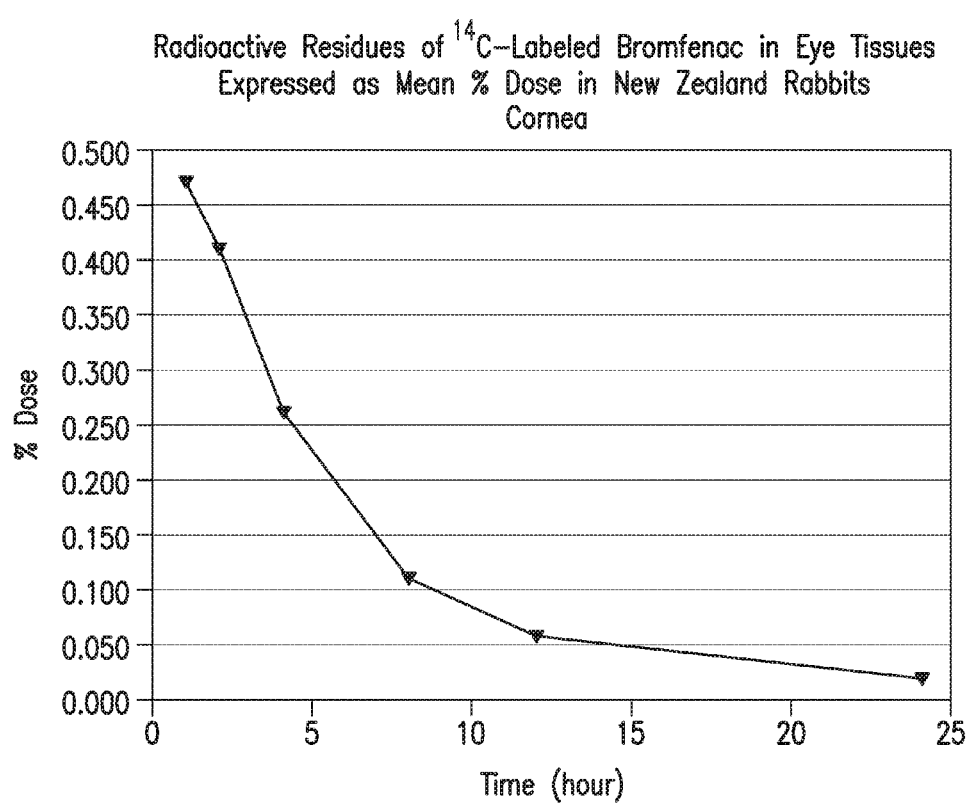
FIG. 17 is a graph of the radioactive residues of $^{14}$C-labeled bromfenac in eye tissues expressed as mean percent dose in New Zealand rabbits cornea.
Figure 18:
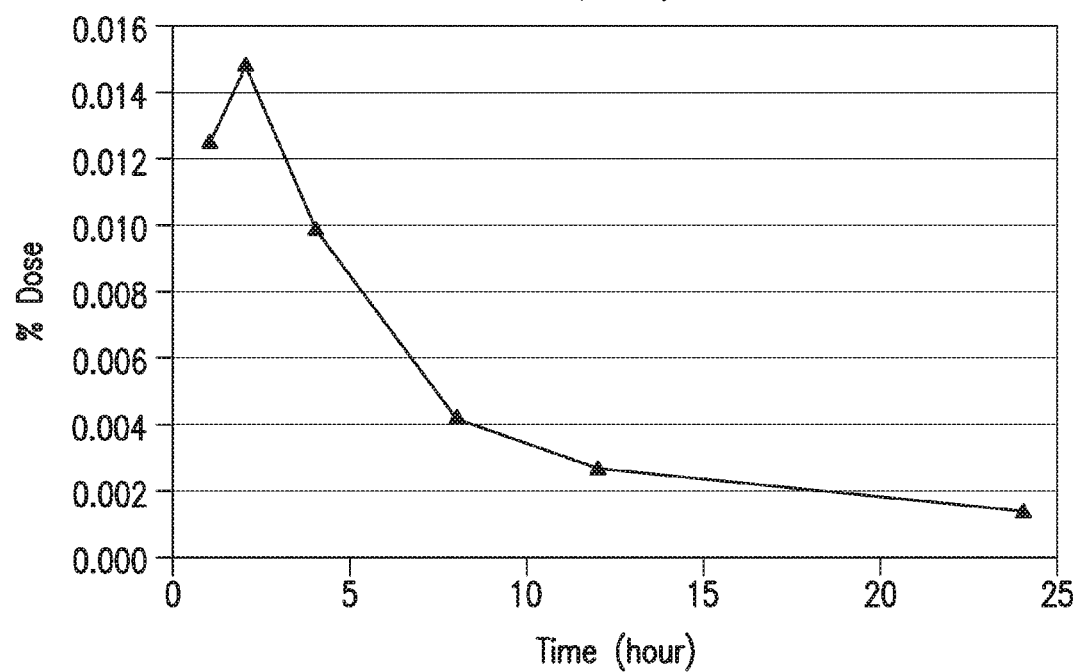
FIG. 18 is a graph of the radioactive residues of $^{14}$C-labeled bromfenac in eye tissues expressed as mean percent dose in New Zealand rabbits iris/ciliary Body.
Figure 19:
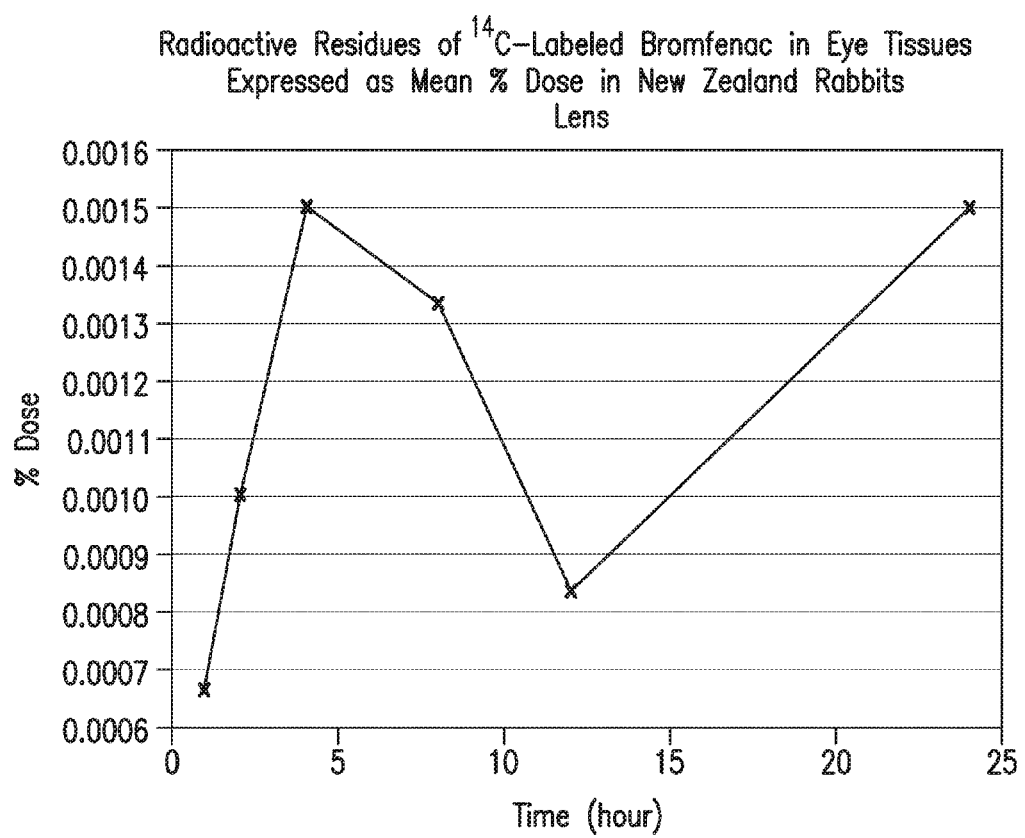
FIG. 19 is a graph of the radioactive residues of $^{14}$C-labeled bromfenac in eye tissues expressed as mean percent dose in New Zealand rabbits lens.
Figure 20:
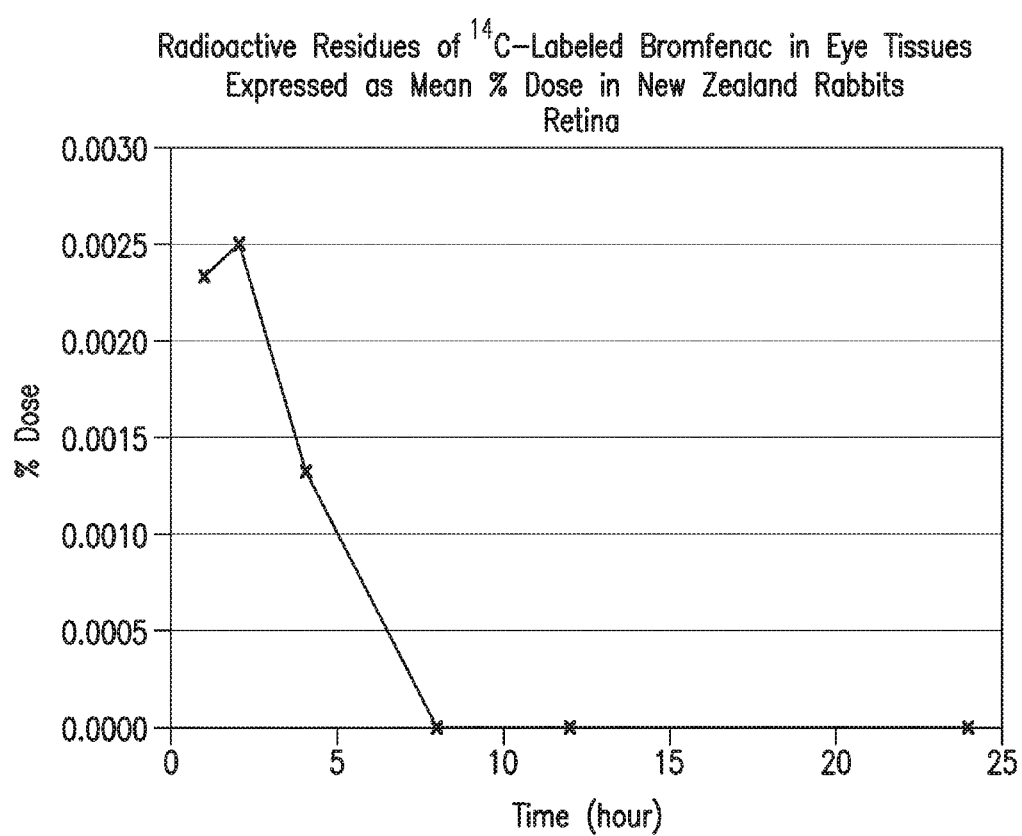
FIG. 20 is a graph of the radioactive residues of $^{14}$C-labeled bromfenac in eye tissues expressed as mean percent dose in New Zealand rabbits retina.
Figure 21:
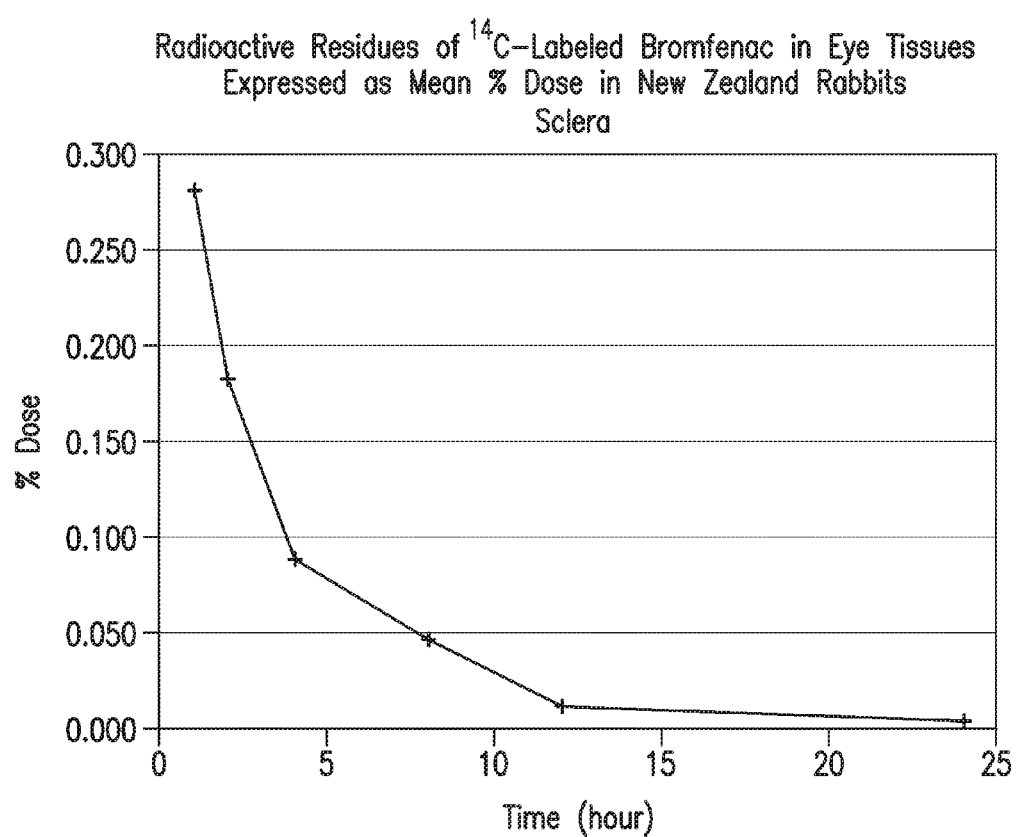
FIG. 21 is a graph of the radioactive residues of $^{14}$C-labeled bromfenac in eye tissues expressed as mean percent dose in New Zealand rabbits sclera.
Figure 22:
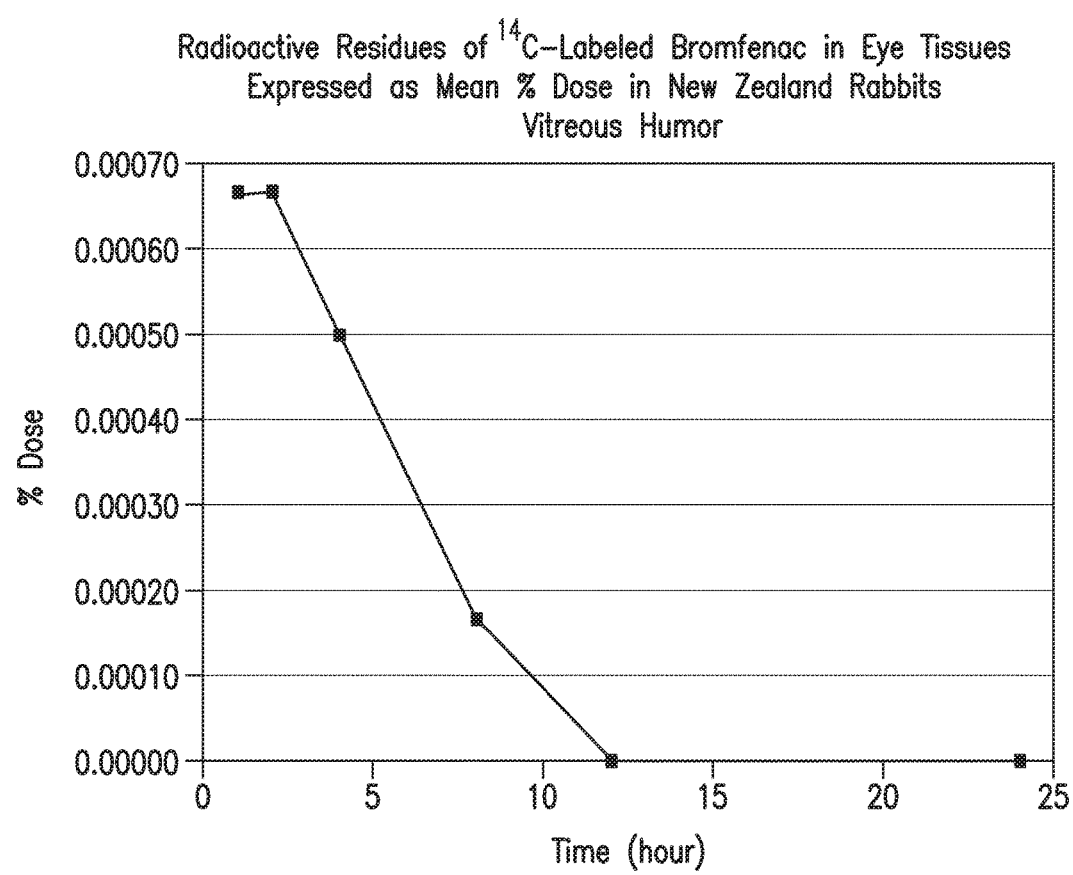
FIG. 22 is a graph of the radioactive residues of $^{14}$C-labeled bromfenac in eye tissues expressed as mean percentage dose in New Zealand rabbits vitreous humor.

In the inventive formulations and methods, by reducing the pH of the formulation, a clinical efficacy equal to or better than the 0.09% bromfenac aqueous formulation was achieved with an aqueous formulation containing less than 0.09% bromfenac. Without being bound by a specific theory, the bromfenac aqueous formulation with reduced pH may have decreased the overall charge of bromfenac and increased bromfenac's hydrophobicity, e.g., a salt such as the sodium salt of bromfenac (FIG. 1A), compared to the bromfenac free base (FIG. 1B) or bromfenac fully protonated form (FIG. 1C), and/or may have increased the octanol-water coefficient (FIG. 2), allowing bromfenac to penetrate environments such as the iris, ciliary body, back of the eye, etc. The enhanced bioavailability enhanced bromfenac's ability to block prostaglandin synthesis, with the result that the patient experienced less pain and less inflammation.

For a given concentration of bromfenac aqueous solution, the pH of the solution significantly impacted the amount of bromfenac that penetrated into targeted ophthalmic tissues, in both the back of the eye such as retina, as well as the front of the eye such as iris and ciliary body, when administered to rabbit eyes.

In one example, three different solutions containing radioactively labeled bromfenac at a concentration of 0.18%, and with respective pH values of 8.3, 7.8 and 7.0, were each administered to rabbit eyes. At varying time points, the amount of bromfenac present in specific ophthalmic tissues was measured. The data below shows the bromfenac levels seen in retinal tissue, i.e., tissue at the back of the eye, two hours following topical (eye drop) administration.

| pH values of 0.18% bromfenac aqueous solutions administered | bromfenac concentration in retina at 2 hr after administration |
|---|---|
| pH 8.3 | 0.01 ppm |
| pH 7.8 | 0.03 ppm |
| pH 7.0 | 0.05 ppm |

The data demonstrated that bromfenac solutions with pH lower than pH 8.3 resulted in higher amounts of bromfenac in the retina.

In another example, aqueous solutions containing radioactively-labeled bromfenac at a concentration of 0.07%, each solution with differing pH values of pH 8.3, pH 7.8 and pH 7.0, respectively, were administered to rabbit eyes. The data below shows the bromfenac levels seen in iris and ciliary body tissue i.e., tissue at the front of the eye, two hours following topical (eye drop) administration.

| pH values of 0.07% bromfenac aqueous solutions administered | bromfenac concentration in iris, ciliary body at 2 hr after administration |
|---|---|
| pH 8.3 | 0.046 ppm |
| pH 7.8 | 0.110 ppm |
| pH 7.0 | 0.154 ppm |

These data demonstrated that reducing the pH of the aqueous bromfenac solution resulted in greater up-take of bromfenac in the iris and ciliary body tissues.

The bromfenac concentration in an ophthalmic solution can be decreased below current levels for treatment of inflammation and pain associated with cataract surgery. By concomitantly decreasing the pH of the formulation, ocular target-tissue levels of bromfenac can be obtained that are comparable to those seen with the current 0.09% bromfenac aqueous formulation.

The data below shows bromfenac levels in rabbit iris and ciliary body tissue two hours following topical (eye drop) administration of 0.09% bromfenac aqueous solution and 0.07% bromfenac aqueous solution at pH 8.3.

| [bromfenac], pH aqueous solution administered | bromfenac concentration in rabbit iris, ciliary body at 2 hr after administration |
| --- | --- |
| 0.09%, pH 8.3 | 0.083 ppm |
| 0.07%, pH 8.3 | 0.046 ppm |

These data demonstrated that reduction in bromfenac concentration from 0.09% to 0.07% resulted in a significant decrease (0.046 ppm vs 0.083 ppm) in bromfenac levels seen in iris and ciliary body tissue.

As shown below, reducing the pH of the 0.07% solution from pH 8.3 to pH 7.8 enabled greater penetration into this tissue, and resulted in higher iris and ciliary body bromfenac levels than seen with the 0.09% bromfenac aqueous formulation (0.110 ppm vs 0.083 ppm).

| [bromfenac], pH aqueous solution administered | bromfenac concentration in rabbit iris, ciliary body at 2 hr after administration |
| --- | --- |
| 0.09%, pH 8.3 | 0.083 ppm |
| 0.07%, pH 7.8 | 0.110 ppm |

An aqueous bromfenac solution formulated for topical ocular administration at pH less than pH 8.3 achieved comparable clinical efficacy at bromfenac concentrations lower than 0.09% bromfenac available as BROMDAY™. One skilled in the art recognizes the increased safety benefit when one achieves comparable clinical effect with reduced concentrations of administered drug.

In one embodiment, the inventive formulations and method are used to increase bromfenac levels in tissues located at the back of the eye. Increased bromfenac concentration, and hence bioavailability, at the back of the eye, as with at the front of the eye, can thus result from either of increasing bromfenac concentration in the administered formulation, and also by decreasing the pH of the administered bromfenac formulation. By increasing bromfenac tissue levels at the back of the eye, increased therapeutic benefit of bromfenac will result as related to therapies associated with the back of the eye.

The bromfenac aqueous formulation at pH less than 8.3 were stable. The excipients in the formulations may include at least one of boric acid, sodium borate (sodium tetraborate decahydrate), USP/NF, sodium sulfite USP, sodium chloride, disodium edetate USP, tyloxapol USP, polysorbate 80, benzalkonium chloride USP/NF, povidone USP, purified water USP, and NaOH (2N), NF. Exemplary formulations are as follows:

EXAMPLE 1

0.05% bromfenac free acid, 0.09% NaCl, 1.5% boric acid, pH 7.0.

EXAMPLE 2

0.08% bromfenac free acid, 0.09% NaCl, 1.5% boric acid, pH 7.0.

EXAMPLE 3

0.05% bromfenac free acid, 1.5% boric acid, 0.09% NaCl, 0.02% tyloxapol, pH 7.0.

EXAMPLE 4

0.08% bromfenac free acid, 0.09% NaCl, 1.5% boric acid, 0.02% tyloxapol, pH 7.0.

EXAMPLE 5

0.06% bromfenac free acid, 1.4% boric acid, 0.74% sodium borate, 0.2% sodium sulfite, 0.02% disodium EDTA, 0.02% tyloxapol, 0.005% BAK, 1.0% povidone pH 7.8.

EXAMPLE 6

0.07% bromfenac free acid, 1.4% boric acid, 0.74% sodium borate, 0.2% sodium sulfite, 0.02% disodium EDTA, 0.02% tyloxapol, 0.005% BAK, 1.0% povidone pH 7.8.

EXAMPLE 7

0.08% bromfenac free acid, 1.4% boric acid, 0.74% sodium borate, 0.2% sodium sulfite, 0.02% disodium EDTA, 0.02% tyloxapol, 0.005% BAK, 1.0% povidone pH 7.8.

EXAMPLE 8

0.06% bromfenac free acid, 1.4% boric acid, 0.74% sodium borate, 0.2% sodium sulfite, 0.02% disodium EDTA, 0.02% tyloxapol, 0.005% BAK, 2.0% povidone pH 7.8.

EXAMPLE 9

0.07% bromfenac free acid, 1.4% boric acid, 0.74% sodium borate, 0.2% sodium sulfite, 0.02% disodium EDTA, 0.02% tyloxapol, 0.005% BAK, 2.0% povidone pH 7.8.

EXAMPLE 10

0.08% bromfenac free acid, 1.4% boric acid, 0.74% sodium borate, 0.2% sodium sulfite, 0.02% disodium EDTA, 0.02% tyloxapol, 0.005% BAK, 2.0% povidone pH 7.8.

Without being bound by a single theory, the stability of formulations at a pH<8.3 was thought to be due to the inclusion of tyloxapol as a solubilizing agent, povidone, and sodium sulfite. In one embodiment, a stable formulation of an aqueous bromfenac solution resulted with pH 7.8. In one embodiment, the concentration of bromfenac as a free acid ranges from 0.02% to <0.20%. In one embodiment, the concentration of tyloxapol ranges from 0.01% to 0.5%. In one embodiment, the concentration of povidone ranges from 0.1% to 2.0%. In one embodiment, the concentration of benzalkonium chloride ranges from 0.0% to 0.010%. In one embodiment, the pH ranges from pH 7 to pH 8. Excipients that may be included in various embodiments of formulations include tyloxapol, povidone, sodium sulfite, benzalkonium chloride, boric acid, sodium borate, disodium edetate, polysorbate 80, hyaluronic acid, buffering agents, other viscosity and suspending agents, e.g., polyvinyl chloride; cellulose polymers, e.g., hydroxypropylmethyl cellulose (HPMC), carboxymethyl cellulose; gums, e.g., xanthan gum, guar gum, and gellan gum; chitosan; carbomers; polycarbophil; sodium hyaluronate; AVICEL™ (microcrystalline cellulose and carboxymethyl cellulose); acacia;

sodium alginate; tragacanth; carrageenan; other nonionic surfactant/stabilizers, e.g., poloxamers; Triton X-100; polyoxyl monostearate; nonoxynols; sorbitan monostearate; glyceryl laurate; cetomacrogol; sugar esters such as sucrose stearate or sucrose palmitate; other preservatives, e.g., chlorhexidine gluconate; alexidine; cetylpyridinium chloride; polyhexamethyline biguanide; methyl/propyl parabens; chlorobutanol; benzyl alcohol; thimerosal; sodium perborate; sodium chlorite.

The inventive formulation and method provided effective bromfenac treatment to a patient in need of such treatment, e.g., a patient after cataract surgery. In use, bromfenac was prepared and topically administered in a formulation that enhanced bromfenac penetration into ocular tissues. This inventive formulation and method permitted a lower bromfenac concentration to be administered than had previously been administered. Advantageously, administration remained at the once daily use currently prescribed for administration with the higher 0.09% BROMDAY™ concentration. Advantageously, administration at the lower concentration provided high efficacy and safety. Thus, the inventive formulation and method provided enhanced bromfenac penetration into ocular tissue when topically administered, compared to the currently available BROMDAY™ formulation and method when topically administered, and while retaining the patient convenience of a once-daily administration and advantageous lower bromfenac concentration dosed to the patient.

EXAMPLE 11

Two multi-center, randomized, double-masked, parallel-group controlled patient studies were performed to determine efficacy of the inventive bromfenac formulations. Four hundred and forty patients who underwent cataract surgery in one eye (unilateral) were assigned randomly to receive either the inventive bromfenac formulation once-daily, or to receive placebo once daily. The placebo was the same formulation as the bromfenac formulation but without bromfenac. Dosing began one day before cataract surgery and continued the day of the surgery and for 14 days following surgery. The proportion of patients experiencing no pain was assessed at day 1 post surgery and throughout the study, i.e., to day 14 following surgery. The proportion of patients with complete absence of ocular inflammation was assessed as early as day 1 post surgery through day 22 post surgery. Ocular inflammation was evaluated using a Summed Ocular Inflammation Score (SOIS). Ocular inflammation assessment was by each of (1) measurement of the number of immune cells in the anterior chamber of the eye (cell measurement), and (2) measurement of the amount of cellular debris in the anterior chamber of the eye (flare measurement). The secondary efficacy endpoint, pain, was evaluated by a pain score from the patient's recorded diary self-assessment, the Ocular Comfort Grading Assessment (OCGA).

Patients self-graded symptoms at each office visit. Symptoms included photophobia, which was the chief symptomatic complaint of cataract surgery. Safety was assessed on variables that included adverse events, ophthalmic evaluation, and diary self-assessment of OCGA.

The study protocol and study results were very similar to those in previous Phase 3 trials for once-daily BROMDAY™; the study using the lower concentration and lower pH formulations had the lowest number of adverse events of any of the bromfenac studies for cataract surgery performed to date.

EXAMPLE 12

Twenty-four hour ocular pharmacokinetics of a formulation of $^{14}$C-labeled bromfenac following topical instillation in New Zealand White rabbit eyes was evaluated. $^{14}$C-labeled bromfenac was analyzed to verify the radioactive purity prior to use. Dosing solutions were prepared and analyzed after dosing to confirm the radiochemical purity of the dosing solution. The radioactive concentration of the dosing solutions was calculated by liquid scintillation counting (LSC). Treatment parameters are summarized below:

| Group | No. | Topical Treatment (Both Eyes) | Dose Volume (per eye) | Necropsy (Time Post-Dose) |
|---|---|---|---|---|
| A | 3 | Bromfenac, 0.07% | 50 µL | 1 hour ± 5 minutes |
| B | 3 | Bromfenac, 0.07% | 50 µL | 2 hours ± 15 minutes |
| C | 3 | Bromfenac, 0.07% | 50 µL | 4 hours ± 15 minutes |
| D | 3 | Bromfenac, 0.07% | 50 µL | 8 hours ± 15 minutes |
| E | 3 | Bromfenac, 0.07% | 50 µL | 12 hours ± 15 minutes |
| F | 3 | Bromfenac, 0.07% | 50 µL | 24 hours ± 15 minutes |

On Day 1, 50 µL of the dosing solution was topically instilled into both eyes of each animal. Animals were weighed at randomization and prior to dosing on Day 1. Animals were euthanized by an intravenous injection of a commercial euthanasia solution at 1 hour±5 minutes, 2 hours±15 minutes, 4 hours±15 minutes, 8 hours±15 minutes, 12 hours±15 minutes, or 24 hours±15 minutes following dosing. After euthanasia, each eye was rinsed with normal saline. Aqueous humor was collected from both eyes and the weight was recorded. The globes were enucleated and frozen in liquid nitrogen. The globes were stored at ≤−70° C. prior to dissection. The iris/ciliary body, lens, vitreous, retina, choroid, sclera, conjunctiva, and cornea were collected from each eye, weighed, and stored at ≤−15° C. prior to analysis. Aqueous humor samples were stored at ≤−15° C. until analyzed.

All radioactivity measurements were performed using a Beckman Liquid Scintillation Spectrometer. The iris/ciliary body, lens, retina, choroid, sclera, conjunctiva, and cornea from each eye were weighed into combustion cones and combusted. Duplicate aliquots of each aqueous humor sample and each vitreous humor sample were transferred to LSC vials using Insta-Gel as the scintillation fluid and the amount of radioactivity was determined.

The mean ppm (µg/g) of drug-derived radioactivity following administration of $^{14}$C-bromfenac was seen in all eye tissues at low levels, with the highest concentrations found in the cornea, conjunctiva, and sclera. The concentrations in the tissues diminished to varying degrees over the 24 hour study period, except for the lens, which exhibited an insignificant increase from the 1 hour time point. The radioactivity detected by LSC in the lens and the vitreous humor was very low and close to background values.

$^{14}$C-labeled bromfenac was used and was stored at ≤−70° C. A diluent (0.07% bomfenac placebo formulation (pH 7.8) was used and was stored at room temperature.

and ophthalmic examination (slit lamp and indirect ophthalmoscopy) was performed on each animal. Fluorescein stain was applied into both eyes of each animal to facilitate the ophthalmic examinations. This deviation had no effect on the outcome of the study. Acceptance criteria for the study were scores of ≤1 for conjunctival congestion and swelling; scores of 0 for all other observation variables. All animals met the acceptance criteria.

Prior to treatment, eighteen animals were weighed and randomly assigned to six treatment groups (Table 1).

TABLE 1

| | | Treatment Groups | | |
|---|---|---|---|---|
| Group | No. | Topical Treatment (Both Eyes) | Dose Volume[1] (per eye) | Necropsy (Time Post-Dose) |
| A | 3 | Bromfenac, 0.07% | 50 μL | 1 hour ± 5 minutes |
| B | 3 | Bromfenac, 0.07% | 50 μL | 2 hours ± 15 minutes |
| C | 3 | Bromfenac, 0.07% | 50 μL | 4 hours ± 15 minutes |
| D | 3 | Bromfenac, 0.07% | 50 μL | 8 hours ± 15 minutes |
| E | 3 | Bromfenac, 0.07% | 50 μL | 12 hours ± 15 minutes |
| F | 3 | Bromfenac, 0.07% | 50 μL | 24 hours ± 15 minutes |

[1]Each 50 μL dose is equivalent to 0.04 mg $^{14}$C-labeled Bromfenac and 6.48 μCi.

| Ingredient | Bromfenac Ophthalmic Solution, 0.07% (pH 7.8) % w/v |
|---|---|
| $^{14}$C Bromfenac Sodium | 0.0805 |
| Boric Acid, USP/NF | 1.40 |
| Sodium Borate (sodium tetraborate decahydrate), USP/NF | 0.74 |
| Sodium Sulfite, USP | 0.20 |
| Disodium Edetate, USP | 0.02 |
| Tyloxapol, USP | 0.02 |
| Benzalkonium Chloride, USP/NF | 0.005 |
| Povidone, USP | 1.00 |
| Purified Water, USP | 100 mL |
| 2N NaOH, NF | pH to 7.8 |

$^{14}$C-labeled bromfenac was analyzed to verify the radioactive purity prior to its use; the radioactive purity was 98.12%.

The dosing solution was prepared by weighing 2.41 mg of $^{14}$C-labeled bromfenac sodium and dissolving into 3 mL diluent to achieve a non-radioactive concentration of 0.7 mg/mL (0.07% w/v) bromfenac free acid, a radioactive concentration of 129.7 μCi/mL, and a pH of 7.8.

The dosing solutions were analyzed after dosing to confirm their radiochemical purity. The radioactive concentrations of the dosing solutions were calculated. Three aliquots (100 μL) of each dosing solution were weighed and brought to a volume of 25 mL with saline. Duplicate aliquots (100 μL) of the resulting diluted solutions were quantitated for radioactivity by liquid scintillation counting (LSC). The post-dose radiochemical purity of the dosing solution was 98.35%. The prepared dosing solutions were stored refrigerated. After dosing, the dosing solutions were stored at ≤−20° C.

Eighteen female New Zealand White rabbits were obtained from The Rabbit Source (Ramona Calif.). Rabbits were at least twelve weeks old and weighed 2.23-3.60 kg at the time of dosing. A pre-treatment physical examination On Day 1, 50 μL of the dosing solution was topically instilled into both eyes of each animal. The dosing solution was instilled into the conjunctival sac using a calibrated pipette, and the eyelid was held closed for 5-10 seconds following the dose. Any dosing solution found at the margin of the eyelid after dosing was recovered with a Lasik spear. The time of each dose administration was recorded.

Animals were observed for mortality/morbidity once during the study except for animals in Group F. Group F animals were observed for mortality/morbidity twice on Day 1 and once on Day 2.

Animals were weighed at randomization and prior to dosing on Day 1.

Animals were euthanized by an intravenous injection of a commercial euthanasia solution at 1 hour±5 minutes, 2 hours±15 minutes, 4 hours±15 minutes, 8 hours±15 minutes, 12 hours±15 minutes, or 24 hours±15 minutes following dosing.

After euthanasia, each eye was rinsed with normal saline. Aqueous humor was collected from both eyes and the weight was recorded. The globes were enucleated and frozen in liquid nitrogen. The globes were stored at ≤−70° C. prior to dissection. The iris/ciliary body, lens, vitreous, retina, choroid, sclera, conjunctiva, and cornea were collected from each eye, weighed, and stored at ≤−15° C. prior to analysis. The start time of necropsy was recorded. Aqueous humor samples were stored at ≤−15° C. until analyzed.

The iris/ciliary body, lens, retina, choroid, sclera, conjunctiva, and cornea from each eye were weighed into combustion cones and combusted with the exception of the left eye from Animal No. 731. The retina, choroid, and cornea from this eye were lost during processing and could not be recovered. No radioactivity data is available for these tissues. Sufficient tissue remained to evaluate the test article for the 24-hour time point and this deviation had a minimal effect on the outcome of the study.

Combusted samples were trapped in $^3$C Cocktail (RJ Harvey) present in LSC vials and the amount of radioactivity determined by LSC. Duplicate aliquots of each aqueous humor sample (approximately 25 μL) were transferred to LSC vials and the amount of radioactivity was determined by LSC using Insta-Gel as the scintillation fluid. Each vitreous humor sample was aliquoted in duplicate (100 µL each) and transferred to LSC vials and the amount of radioactivity was determined by LSC using Insta-Gel as the scintillation fluid. The amount of radioactivity was determined by LSC. If samples were frozen prior to analysis, they were thawed and properly mixed prior to removing aliquots for analysis. Remaining samples were stored at ≤−20° C.

All radioactivity measurements were performed using a Beckman Liquid Scintillation Spectrometer. Counting time was either at a statistical accuracy of ±2% or a maximum of 10 minutes, whichever came first. The spectrometer was programmed to automatically subtract background and convert cpm to dpm. If the coefficient of variation of the radioactivity measurement of the aliquots of a sample differed by more than 20 percent, the sample was realiquoted and reanalyzed, if sufficient sample was available. Any radioactivity measurement of less than 100 dpm was considered close to background and was not repeated.

When applicable, the mean (x) and standard deviation (SD) for each tissue were used to characterize the data (i.e., radioactivity measurement, % dose, etc.). All other data collected were evaluated by inspection only.

Mortality data and body weights are presented in Table 2.

TABLE 2

Body Weights and Mortality Data

| Group | Animal No. | Day 1 Weight (kg) | Mortality/Morbidity[1] |
|---|---|---|---|
| A | 640 | 2.39 | 0/3 |
|   | 719 | 3.12 |   |
|   | 733 | 2.78 |   |
| B | 636 | 2.23 | 0/3 |
|   | 727 | 3.12 |   |
|   | 732 | 3.40 |   |
| C | 634 | 2.43 | 0/3 |
|   | 718 | 3.20 |   |
|   | 725 | 2.75 |   |
| D | 637 | 2.35 | 0/3 |
|   | 644 | 2.46 |   |
|   | 724 | 3.60 |   |
| E | 641 | 2.43 | 0/3 |
|   | 726 | 3.42 |   |
|   | 734 | 2.77 |   |
| F | 642 | 2.38 | 0/3 |
|   | 645 | 2.51 |   |
|   | 731 | 3.04 |   |

[1]Mortality is expressed as the number of animals found dead or euthanized prior to scheduled euthanasia/number of animals in group.

There was no mortality, and all animals were within the weight range.

Radioactive residues of $^{14}$C-labeled bromfenac, expressed as mean ppm (µg-eq/g) and mean percent of dose, in eye tissue are presented in Tables 3 and 4, respectively, and FIGS. 3-12 and FIGS. 13-22, respectively.

TABLE 3

Radioactive Residues of $^{14}$C-labeled Bromfenac in Eye Tissues Expressed as Mean ppm (µg-eq/g) in New Zealand Rabbits

| | Group A, 1 hr. Animal No. | | | | | | | Group B, 2 hr. Animal No. | | | | | | |
|---|---|---|---|---|---|---|---|---|---|---|---|---|---|---|
| | 640 | | 719 | | 733 | | | 636 | | 727 | | 732 | | |
| Tissues | OD | OS | OD | OS | OD | OS | Mean ± SD | OD | OS | OD | OS | OD | OS | Mean ± SD |
| Aqueous Humor | 0.045 | 0.062 | 0.043 | 0.071 | 0.045 | 0.076 | 0.057 0.014 | 0.051 | 0.066 | 0.065 | 0.069 | 0.072 | 0.060 | 0.064 0.008 |
| Vitreous Humor | 0.000 | 0.000 | 0.000 | 0.000 | 0.000 | 0.000 | 0.000 0.000 | 0.000 | 0.000 | 0.000 | 0.000 | 0.000 | 0.000 | 0.000 0.000 |
| Iris/Ciliary Body | 0.085 | 0.071 | 0.061 | 0.083 | 0.060 | 0.101 | 0.077 0.016 | 0.075 | 0.103 | 0.085 | 0.090 | 0.077 | 0.060 | 0.082 0.015 |
| Lens | 0.000 | 0.000 | 0.000 | 0.001 | 0.000 | 0.001 | 0.001 0.000 | 0.001 | 0.001 | 0.001 | 0.001 | 0.001 | 0.001 | 0.001 0.000 |
| Retina | 0.013 | 0.011 | 0.011 | 0.022 | 0.007 | 0.007 | 0.012 0.006 | 0.017 | 0.013 | 0.008 | 0.008 | 0.010 | 0.007 | 0.010 0.004 |
| Choroid | 0.058 | 0.067 | 0.052 | 0.065 | 0.037 | 0.043 | 0.054 0.012 | 0.051 | 0.041 | 0.041 | 0.036 | 0.031 | 0.017 | 0.036 0.012 |
| Sclera | 0.469 | 0.562 | 0.422 | 0.599 | 0.392 | 0.419 | 0.477 0.085 | 0.372 | 0.401 | 0.184 | 0.234 | 0.267 | 0.134 | 0.265 0.104 |
| Cornea | 2.182 | 2.156 | 1.939 | 2.874 | 2.008 | 3.253 | 2.402 0.534 | 1.669 | 2.139 | 1.789 | 2.113 | 2.689 | 1.591 | 1.998 0.407 |
| Conjunctiva | 1.063 | 1.304 | 0.896 | 1.054 | 1.000 | 0.978 | 1.049 0.138 | 0.656 | 0.750 | 0.361 | 0.250 | 0.610 | 0.283 | 0.485 0.213 |

| | Group C, 4 hr. Animal No. | | | | | | | Group D, 8 hr. Animal No. | | | | | | |
|---|---|---|---|---|---|---|---|---|---|---|---|---|---|---|
| | 634 | | 718 | | 725 | | | 637 | | 644 | | 724 | | |
| Tissues | OD | OS | OD | OS | OD | OS | Mean ± SD | OD | OS | OD | OS | OD | OS | Mean ± SD |
| Aqueous Humor | 0.035 | 0.045 | 0.041 | 0.080 | 0.030 | 0.064 | 0.049 0.019 | 0.015 | 0.015 | 0.018 | 0.008 | 0.026 | 0.018 | 0.017 0.006 |
| Vitreous Humor | 0.000 | 0.000 | 0.000 | 0.000 | 0.000 | 0.000 | 0.000 0.000 | 0.000 | 0.000 | 0.000 | 0.000 | 0.000 | 0.000 | 0.000 0.000 |
| Iris/Ciliary Body | 0.042 | 0.051 | 0.047 | 0.091 | 0.042 | 0.072 | 0.058 0.020 | 0.021 | 0.022 | 0.026 | 0.020 | 0.038 | 0.031 | 0.026 0.007 |
| Lens | 0.001 | 0.001 | 0.001 | 0.003 | 0.001 | 0.002 | 0.001 0.001 | 0.001 | 0.002 | 0.002 | 0.001 | 0.001 | 0.001 | 0.001 0.000 |
| Retina | 0.007 | 0.006 | 0.006 | 0.009 | 0.006 | 0.008 | 0.007 0.001 | 0.002 | 0.001 | 0.003 | 0.001 | 0.002 | 0.002 | 0.002 0.001 |
| Choroid | 0.030 | 0.034 | 0.025 | 0.049 | 0.020 | 0.032 | 0.032 0.010 | 0.009 | 0.006 | 0.016 | 0.006 | 0.016 | 0.010 | 0.010 0.005 |

TABLE 3-continued

Radioactive Residues of $^{14}$C-labeled Bromfenac in Eye Tissues Expressed as Mean ppm (μg-eq/g) in New Zealand Rabbits

| | | | | | | | | | | | | | | | | |
|---|---|---|---|---|---|---|---|---|---|---|---|---|---|---|---|---|
| Sclera | 0.134 | 0.160 | 0.109 | 0.259 | 0.076 | 0.157 | 0.149 | 0.062 | 0.075 | 0.024 | 0.171 | 0.023 | 0.111 | 0.045 | 0.075 | 0.058 |
| Cornea | 0.744 | 0.859 | 1.077 | 2.114 | 0.929 | 1.590 | 1.219 | 0.529 | 0.367 | 0.301 | 0.463 | 0.226 | 0.848 | 0.619 | 0.471 | 0.230 |
| Conjunctiva | 0.282 | 0.523 | 0.168 | 0.422 | 0.154 | 0.578 | 0.355 | 0.181 | 0.175 | 0.048 | 0.139 | 0.101 | 0.243 | 0.115 | 0.137 | 0.067 |

| | Group E, 12 hr. Animal No. | | | | | | | Group F, 24 hr. Animal No. | | | | | | | |
|---|---|---|---|---|---|---|---|---|---|---|---|---|---|---|---|
| | 641 | | 726 | | 734 | | | 642 | | 645 | | 731 | | | |
| Tissues | OD | OS | OD | OS | OD | OS | Mean ± SD | OD | OS | OD | OS | OD | OS[1] | Mean ± SD | |
| Aqueous Humor | 0.004 | 0.004 | 0.003 | 0.006 | 0.008 | 0.008 | 0.006 0.002 | 0.001 | 0.001 | 0.002 | 0.002 | 0.001 | 0.001 | 0.001 0.001 | |
| Vitreous Humor | 0.000 | 0.000 | 0.000 | 0.000 | 0.000 | 0.000 | 0.000 0.000 | 0.000 | 0.000 | 0.000 | 0.000 | 0.000 | 0.000 | 0.000 0.000 | |
| Iris/Ciliary Body | 0.015 | 0.017 | 0.015 | 0.020 | 0.016 | 0.019 | 0.017 0.002 | 0.008 | 0.011 | 0.021 | 0.009 | 0.008 | 0.006 | 0.010 0.005 | |
| Lens | 0.001 | 0.001 | 0.000 | 0.000 | 0.001 | 0.001 | 0.001 0.000 | 0.002 | 0.002 | 0.002 | 0.002 | 0.001 | 0.001 | 0.002 0.001 | |
| Retina | 0.001 | 0.001 | 0.001 | 0.001 | 0.001 | 0.001 | 0.001 0.000 | 0.001 | 0.001 | 0.000 | 0.001 | 0.001 | N/A | 0.001 0.000 | |
| Choroid | 0.003 | 0.005 | 0.005 | 0.005 | 0.006 | 0.005 | 0.005 0.001 | 0.001 | 0.001 | 0.002 | 0.002 | 0.004 | N/A | 0.002 0.001 | |
| Sclera | 0.012 | 0.025 | 0.015 | 0.024 | 0.018 | 0.015 | 0.018 0.005 | 0.003 | 0.004 | 0.006 | 0.035 | 0.005 | 0.004 | 0.009 0.013 | |
| Cornea | 0.146 | 0.244 | 0.121 | 0.217 | 0.381 | 0.257 | 0.228 0.092 | 0.058 | 0.042 | 0.073 | 0.167 | 0.062 | N/A | 0.080 0.050 | |
| Conjunctiva | 0.033 | 0.183 | 0.038 | 0.054 | 0.091 | 0.071 | 0.079 0.056 | 0.018 | 0.016 | 0.020 | 0.112 | 0.010 | 0.012 | 0.031 0.040 | |

[1]Retina, choroid, and cornea of OS for Animal No. 731 were lost during processing and could not be recovered. No radioactivity data is available for these samples.

TABLE 4

Radioactive Residues of $^{14}$C-labeled Bromfenac in Eye Tissues Expressed as Mean Percent Dose in New Zealand Rabbits

| | Group A, 1 hr. Animal No. | | | | | | | Group B, 2 hr. Animal No. | | | | | | | |
|---|---|---|---|---|---|---|---|---|---|---|---|---|---|---|---|
| | 640 | | 719 | | 733 | | | 636 | | 727 | | 732 | | | |
| Tissues | OD | OS | OD | OS | OD | OS | Mean ± SD | OD | OS | OD | OS | OD | OS | Mean ± SD | |
| Aqueous Humor | 0.034 | 0.041 | 0.039 | 0.066 | 0.039 | 0.061 | 0.034 0.041 | 0.036 | 0.048 | 0.059 | 0.064 | 0.074 | 0.052 | 0.056 0.013 | |
| Vitreous Humor | 0.001 | 0.001 | 0.001 | 0.000 | 0.000 | 0.001 | 0.001 0.001 | 0.001 | 0.001 | 0.000 | 0.001 | 0.001 | 0.000 | 0.001 0.001 | |
| Iris/Ciliary Body | 0.010 | 0.009 | 0.011 | 0.019 | 0.010 | 0.016 | 0.010 0.009 | 0.012 | 0.015 | 0.013 | 0.015 | 0.020 | 0.014 | 0.015 0.003 | |
| Lens | 0.000 | 0.000 | 0.001 | 0.001 | 0.001 | 0.001 | 0.000 0.000 | 0.001 | 0.001 | 0.001 | 0.001 | 0.001 | 0.001 | 0.001 0.000 | |
| Retina | 0.002 | 0.003 | 0.002 | 0.005 | 0.001 | 0.001 | 0.002 0.003 | 0.003 | 0.003 | 0.002 | 0.002 | 0.003 | 0.002 | 0.003 0.001 | |
| Choroid | 0.004 | 0.005 | 0.006 | 0.005 | 0.003 | 0.004 | 0.004 0.005 | 0.005 | 0.003 | 0.004 | 0.003 | 0.003 | 0.001 | 0.003 0.001 | |
| Sclera | 0.242 | 0.297 | 0.254 | 0.376 | 0.255 | 0.268 | 0.242 0.297 | 0.233 | 0.250 | 0.116 | 0.144 | 0.224 | 0.114 | 0.180 0.062 | |
| Cornea | 0.368 | 0.390 | 0.410 | 0.605 | 0.436 | 0.632 | 0.368 0.390 | 0.272 | 0.338 | 0.397 | 0.459 | 0.604 | 0.396 | 0.411 0.114 | |
| Conjunctiva | 0.293 | 0.426 | 0.287 | 0.346 | 0.440 | 0.390 | 0.293 0.426 | 0.198 | 0.264 | 0.170 | 0.093 | 0.316 | 0.145 | 0.198 0.081 | |
| Total | 0.954 | 1.172 | 1.011 | 1.423 | 1.185 | 1.374 | 1.187 0.188 | 0.761 | 0.923 | 0.762 | 0.782 | 1.246 | 0.725 | 0.867 0.198 | |

| | Group C, 4 hr. Animal No. | | | | | | | Group D, 8 hr. Animal No. | | | | | | | |
|---|---|---|---|---|---|---|---|---|---|---|---|---|---|---|---|
| | 634 | | 718 | | 725 | | | 637 | | 644 | | 724 | | | |
| Tissues | OD | OS | OD | OS | OD | OS | Mean ± SD | OD | OS | OD | OS | OD | OS | Mean ± SD | |
| Aqueous Humor | 0.028 | 0.036 | 0.036 | 0.071 | 0.025 | 0.053 | 0.042 0.017 | 0.009 | 0.009 | 0.011 | 0.005 | 0.029 | 0.020 | 0.014 0.009 | |
| Vitreous Humor | 0.000 | 0.001 | 0.001 | 0.001 | 0.000 | 0.000 | 0.001 0.001 | 0.000 | 0.000 | 0.000 | 0.000 | 0.000 | 0.001 | 0.000 0.000 | |
| Iris/Ciliary Body | 0.007 | 0.009 | 0.008 | 0.015 | 0.007 | 0.013 | 0.010 0.003 | 0.003 | 0.003 | 0.003 | 0.003 | 0.007 | 0.006 | 0.004 0.002 | |
| Lens | 0.001 | 0.001 | 0.001 | 0.003 | 0.001 | 0.002 | 0.002 0.001 | 0.001 | 0.002 | 0.001 | 0.001 | 0.002 | 0.001 | 0.001 0.001 | |
| Retina | 0.002 | 0.001 | 0.001 | 0.002 | 0.001 | 0.001 | 0.001 0.001 | 0.000 | 0.000 | 0.000 | 0.000 | 0.000 | 0.000 | 0.000 0.000 | |
| Choroid | 0.003 | 0.003 | 0.002 | 0.005 | 0.001 | 0.003 | 0.003 0.001 | 0.001 | 0.000 | 0.001 | 0.000 | 0.002 | 0.001 | 0.001 0.001 | |
| Sclera | 0.071 | 0.086 | 0.064 | 0.158 | 0.047 | 0.101 | 0.088 0.039 | 0.043 | 0.015 | 0.087 | 0.012 | 0.087 | 0.034 | 0.046 0.034 | |
| Cornea | 0.141 | 0.158 | 0.235 | 0.458 | 0.184 | 0.395 | 0.262 0.133 | 0.061 | 0.055 | 0.082 | 0.038 | 0.244 | 0.170 | 0.108 0.081 | |
| Conjunctiva | 0.137 | 0.198 | 0.081 | 0.190 | 0.050 | 0.198 | 0.142 0.064 | 0.039 | 0.013 | 0.043 | 0.022 | 0.134 | 0.064 | 0.053 0.044 | |
| Total | 0.390 | 0.493 | 0.429 | 0.903 | 0.316 | 0.766 | 0.550 0.232 | 0.157 | 0.097 | 0.228 | 0.081 | 0.505 | 0.297 | 0.228 0.158 | |

TABLE 4-continued

Radioactive Residues of $^{14}$C-labeled Bromfenac in Eye Tissues Expressed as Mean Percent Dose in New Zealand Rabbits

| | Group E, 12 hr. Animal No. | | | | | | | Group F, 24 hr. Animal No. | | | | | | | |
|---|---|---|---|---|---|---|---|---|---|---|---|---|---|---|---|
| | 641 | | 726 | | 734 | | | 642 | | 645 | | 731 | | | |
| Tissues | OD | OS | OD | OS | OD | OS | Mean ± SD | OD | OS | OD | OS | OD | OS[1] | Mean ± SD | |
| Aqueous Humor | 0.002 | 0.003 | 0.004 | 0.007 | 0.005 | 0.006 | 0.005 0.002 | 0.001 | 0.001 | 0.001 | 0.002 | 0.001 | 0.001 | 0.001 | 0.000 |
| Vitreous Humor | 0.000 | 0.000 | 0.000 | 0.000 | 0.000 | 0.000 | 0.000 0.000 | 0.000 | 0.000 | 0.000 | 0.000 | 0.000 | 0.000 | 0.000 | 0.000 |
| Iris/Ciliary Body | 0.002 | 0.002 | 0.003 | 0.004 | 0.002 | 0.003 | 0.003 0.001 | 0.001 | 0.001 | 0.003 | 0.001 | 0.001 | 0.001 | 0.001 | 0.001 |
| Lens | 0.001 | 0.001 | 0.000 | 0.001 | 0.001 | 0.001 | 0.001 0.000 | 0.002 | 0.001 | 0.002 | 0.002 | 0.001 | 0.001 | 0.002 | 0.001 |
| Retina | 0.000 | 0.000 | 0.000 | 0.000 | 0.000 | 0.000 | 0.000 0.000 | 0.000 | 0.000 | 0.000 | 0.000 | 0.000 | N/A | 0.000 | 0.000 |
| Choroid | 0.000 | 0.000 | 0.000 | 0.001 | 0.000 | 0.001 | 0.000 0.001 | 0.000 | 0.000 | 0.000 | 0.000 | 0.000 | N/A | 0.000 | 0.000 |
| Sclera | 0.007 | 0.015 | 0.011 | 0.019 | 0.011 | 0.008 | 0.012 0.004 | 0.002 | 0.002 | 0.004 | 0.012 | 0.003 | 0.003 | 0.004 | 0.004 |
| Cornea | 0.026 | 0.045 | 0.036 | 0.073 | 0.091 | 0.066 | 0.056 0.025 | 0.013 | 0.009 | 0.018 | 0.040 | 0.015 | N/A | 0.019 | 0.012 |
| Conjunctiva | 0.015 | 0.069 | 0.020 | 0.027 | 0.034 | 0.021 | 0.031 0.020 | 0.006 | 0.006 | 0.007 | 0.027 | 0.005 | 0.005 | 0.009 | 0.009 |
| Total | 0.053 | 0.135 | 0.074 | 0.132 | 0.144 | 0.106 | 0.107 0.037 | 0.025 | 0.020 | 0.035 | 0.084 | 0.026 | 0.011 | 0.034 | 0.026 |

[1]Retina, choroid, and cornea of OS for Animal No. 731 were lost during processing and could not be recovered. No radioactivity data is available for these samples.

The mean ppm (µg/g) of drug-derived radioactivity following administration of $^{14}$C-bromfenac was seen in all eye tissues at low levels, with the highest concentrations in the cornea, conjunctiva, and sclera. The tissue concentrations diminished to varying degrees over 24 hours, except for the lens, which exhibited an insignificant increase from the 1 hour time point. The radioactivity detected by LSC in the lens and the vitreous humor was very low and close to background values.

The mean ppm (µg/g) of drug-derived radioactivity following administration of $^{14}$C-bromfenac was seen in all tissues of the eyes at low levels, with the highest concentrations found in the cornea, conjunctiva, and sclera. The concentrations in the tissues diminished to varying degrees over the 24 hour study period, except for the lens, which exhibited a very insignificant increase from the 1 hour time point. The radioactivity detected by LSC in the lens and the vitreous humor was very low and close to background values.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. An aqueous composition formulated for topical ocular administration, the composition comprising bromfenac as the only active at 0.07% w/v and 1.0% w/v povidone in a formulation buffered at a pH between pH≥6.0 and pH<8.0.

2. The composition of claim 1 at pH≥7.0 and ≤7.8.

3. The composition of claim 1 containing 0.07% w/v bromfenac at pH 7.0.

4. The composition claim 1 containing 0.07% w/v bromfenac at pH 7.1.

5. The composition of claim 1 containing 0.07% w/v bromfenac at pH 7.2.

6. The composition of claim 1 containing 0.07% w/v bromfenac at pH 7.3.

7. The composition of claim 1 containing 0.07% w/v bromfenac at pH 7.4.

8. The composition of claim 1 containing 0.07% w/v bromfenac at pH 7.5.

9. The composition of claim 1 containing 0.07% w/v bromfenac at pH 7.6.

10. The composition of claim 1 containing 0.07% w/v bromfenac at pH 7.7.

11. The composition of claim 1 containing 0.07% w/v bromfenac at pH 7.8.

12. The composition of claim 1 further comprising at least one of tyloxapol, sodium sulfite, or benzalkonium chloride.

13. The composition of claim 1 further comprising at least one of tyloxapol at a concentration of 0.01% w/v to 0.5% w/v, sodium sulfite, or benzalkonium chloride at a concentration of ≤0.01% w/v.

* * * * *

UNITED STATES PATENT AND TRADEMARK OFFICE
CERTIFICATE OF CORRECTION

PATENT NO. : 10,085,958 B2
APPLICATION NO. : 15/343457
DATED : October 2, 2018
INVENTOR(S) : Angel Padilla et al.

Page 1 of 1

It is certified that error appears in the above-identified patent and that said Letters Patent is hereby corrected as shown below:

In the Claims

At Column 26, Claim number 4, Line number 28, after "composition" insert --of--

Signed and Sealed this
First Day of January, 2019

Andrei Iancu
*Director of the United States Patent and Trademark Office*